(12) United States Patent
Yodfat et al.

(10) Patent No.: US 10,369,281 B2
(45) Date of Patent: Aug. 6, 2019

(54) DEVICES, SYSTEMS AND METHODS FOR ADJUSTING FLUID DELIVERY PARAMETERS

(75) Inventors: Ofer Yodfat, Modi'in (IL); Gali Shapira, Haifa (IL); Iddo Gescheit, Tel-Aviv (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1991 days.

(21) Appl. No.: 13/395,010

(22) PCT Filed: Sep. 7, 2010

(86) PCT No.: PCT/IL2010/000744
§ 371 (c)(1),
(2), (4) Date: May 21, 2012

(87) PCT Pub. No.: WO2011/030343
PCT Pub. Date: Mar. 17, 2011

(65) Prior Publication Data
US 2012/0226259 A1 Sep. 6, 2012

Related U.S. Application Data

(60) Provisional application No. 61/240,326, filed on Sep. 8, 2009, provisional application No. 61/241,939, filed on Sep. 13, 2009.

(51) Int. Cl.
*G01N 33/48* (2006.01)
*A61M 5/168* (2006.01)
(Continued)

(52) U.S. Cl.
CPC .... *A61M 5/16877* (2013.01); *A61M 5/14244* (2013.01); *A61M 5/16804* (2013.01);
(Continued)

(58) Field of Classification Search
CPC .. A61M 2005/14513; A61M 205/3317; A61M 2205/702; G06F 19/3456; G06F 19/345; G06F 19/3481
See application file for complete search history.

(56) References Cited

U.S. PATENT DOCUMENTS

2005/0049179 A1 3/2005 Davidson et al.
2007/0062251 A1 3/2007 Anex
(Continued)

FOREIGN PATENT DOCUMENTS

WO 2008048556 A2 4/2008
WO 2009075925 A1 6/2009

OTHER PUBLICATIONS

International Search Report for Application No. PCT/IL2010/000744 dated Jan. 6, 2011.

*Primary Examiner* — Larry D Riggs, II
(74) *Attorney, Agent, or Firm* — Dinsmore & Shohl, LLP

(57) ABSTRACT

Devices, systems and methods for adjusting fluid delivery based on past or historical fluid delivery data and/or personal parameters of a user are disclosed. Devices, and corresponding systems and methods, may comprise a dispensing unit configured to deliver a fluid from a reservoir into the body of a user and a processor having instructions operating thereon to retrieve data relating to one or more time windows from a memory, assess a correction delivery for the one or more time windows based on the data, determine a new CIR value for the one or more time windows if the correction delivery regularly follows a meal bolus and/or determine a new basal delivery profile for the one or more time windows if the correction delivery regularly precedes a meal bolus.

29 Claims, 11 Drawing Sheets

(51) Int. Cl.
*A61M 5/142* (2006.01)
*A61M 5/172* (2006.01)
*G16H 40/63* (2018.01)
*G16H 20/17* (2018.01)

(52) U.S. Cl.
CPC ........ *A61M 5/16831* (2013.01); *A61M 5/172* (2013.01); *G16H 20/17* (2018.01); *G16H 40/63* (2018.01); *A61M 2205/3569* (2013.01)

(56) References Cited

U.S. PATENT DOCUMENTS

2008/0172031 A1 7/2008 Blomquist
2008/0206799 A1 8/2008 Blomquist

DEVICES, SYSTEMS AND METHODS FOR ADJUSTING FLUID DELIVERY PARAMETERS

CROSS-REFERENCE TO RELATED APPLICATIONS

The present application is a 35 U.S.C. § 371 national stage entry of PCT/IL2010/000744, which has an international filing date of Sep. 7, 2010 and claims priority to U.S. Provisional Application Ser. No. 61/240,326, filed on Sep. 8, 2009 and entitled "Device and Method for Adjusting Insulin Delivery" and U.S. Provisional Patent Application Ser. No. 61/241,939, filed on Sep. 13, 2009 and entitled "Device and Method for Delivery and Quantification of Insulin Dosages," the disclosures of which are incorporated herein by reference in their entireties.

FIELD

Devices, systems and methods for sustained medical infusion of therapeutic fluids (e.g., insulin) are disclosed herein. Some embodiments relate to portable infusion devices and methods for adjusting delivery of therapeutic fluids according to delivery history. Some embodiments relate to skin securable insulin dispensing devices and methods for adjusting basal delivery profiles and/or a user's personal parameters in accordance with previous correction bolus doses and delivery suspensions.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin in correspondence with blood glucose levels, maintaining near-constant glucose levels in the body.

Much of the burden of the disease to patients and to health care resources is due to the long-term tissue complications, which affect both small blood vessels (microangiopathy, causing eye, kidney and nerve damage) and large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbA1c) [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining euglycemia by frequent glucose measurements and adjustment of insulin delivery accordingly is of utmost importance.

Conventional insulin pumps deliver rapid-acting insulin 24 hours a day through a catheter placed under the skin. The insulin total daily dose ("TDD") is typically divided into basal and bolus doses. Basal doses of insulin are delivered continuously over 24 hours to keep blood glucose concentrations within acceptable ranges between meal times and overnight. The amount of insulin continuously delivered over a specific time period may be referred to as the basal rate. In conventional insulin pumps, diurnal basal rates can be pre-programmed or manually changed according to different daily activities. Continuous insulin delivery can be suspended for a predetermined time period to deal with hypoglycemia or with impending hypoglycemia (e.g., when a continuous glucose monitor ("CGM") alerts of such a predicted situation).

Bolus doses may be delivered during episodes of high blood glucose concentrations and referred to as a "correction bolus" or "CB" or, when delivered before, during or after meals to counteract carbohydrate loads, referred to as a "meal bolus" or "MB." Conventional parameters used for determining proper bolus doses may include without limitation at least one of the following:

the amount of carbohydrates consumed or to be consumed ("TC");

the carbohydrate-to-insulin ratio ("CIR")—the amount of carbohydrates balanced by one unit of insulin measured in grams per unit of insulin. A high or low CIR value indicates that a high or low amount of carbohydrates may be "covered" by one unit of insulin, respectively;

insulin sensitivity ("IS")—the amount of blood glucose lowered by one unit of insulin measured in milligrams per deciliter (mg/dL) per unit of insulin;

current blood glucose levels ("CBG") measured in mg/dL;

target blood glucose levels ("TBG")—a desired blood glucose level measured in mg/dL; and/or residual insulin ("RI")—the amount of stored active insulin remaining in the body of a patient after delivery of a bolus dose (also known as "bolus on board" or BOB).

Additional parameters (e.g., glycemic index) can be also used, and different units can be used, for example "mmol" instead of "mg/dL".

Conventional insulin pumps may provide bolus dose recommendations based on one or more of the above-listed parameters. For example, an MB dose may be calculated by dividing the amount of carbohydrates (TC) by the CIR. In U.S. Pat. No. 6,936,029 to Mann et al., a recommended bolus dose is calculated based on all of the above-listed parameters as follows:

$$\underbrace{(TC/CIR)}_{\text{"Food Estimate"}} + \underbrace{[(CBG - TBG)/IS]}_{\text{"Correction Estimate"}} - RI = \text{Recommended Bolus Dose}$$

Some of these parameters are also considered in the bolus dose recommendation feature described in U.S. Patent Application Publication No. US2008/0234663 to Yodfat et al. and International Publication No. WO 2009/133558, the disclosures of which are incorporated herein by reference in their entireties. These publications describe this feature as comprising sets of grids of ranges of carbohydrate amounts and blood glucose levels, wherein each grid may correspond to a different combination of IS, CIR and/or TBG. The publications also note that additional grids may correspond to selected bolus doses and RI values. According to some embodiments in these publications, a final recommended bolus dose may be related to a value substantially similar to the selected bolus dose minus the RI.

IS and CIR values, in particular, are often used to initially set the bolus calculator of many existing pumps or when a user calculates a bolus dose. For Type 1 diabetes patients using rapid-acting insulin, IS values may be determined according to the "2200 to 1600 Rules," which are commonly used to determine a correction factor that provides guidance as to what CB dose (for example) should be used to reduce high blood glucose concentrations. For example, the 1800 Rule shows how much blood glucose concentrations may drop per unit of rapid-acting insulin (such as insulin aspart (NovoLog®) and/or insulin lispro (Humalog®)) and the 1500 Rule provides a similar indication per unit of regular insulin (e.g., Humulin® R, Novolin® R). The IS value is established by dividing the appropriate Rule by the TDD (e.g., if the TDD is 40 U and the 1800 Rule is applied, the IS value would be 1800 divided by 40, or 45 mg/dL per unit of insulin).

Similarly, Type 1 diabetes patients may determine the CIR using the "450 to 500 Rules," wherein the 500 Rule is one way to estimate how many grams of carbohydrates will be covered by one unit of rapid-acting insulin (such as aspart (NovoLog®) and/or insulin lispro (Humalog®)). The CIR is established by dividing the appropriate Rule by the TDD (e.g., if the TDD is 40 U and the 450 Rule is used, the CIR would be 450 divided by 40, or about 11 grams per unit of insulin).

Notwithstanding the well-accepted use of the abovementioned "Rules," drawbacks exist, including without limitation:

inaccuracies in the established IS and CIR due to the limited number of applicable Rules; and the TDD applied to the Rules is not always known and/or accurate.

Excessive delivery of insulin doses (i.e., over-dose) or excessive insulin delivery suspensions (DS's) (i.e., under-dose) may imply inadequate insulin regime, such as fault initial insulin delivery programming of basal and/or bolus doses resulting in poor glycemic control (including hypo- and hyper-glycemia). For example, excessive deliveries of CB doses to account for high blood glucose concentrations might stem from an inadequate basal rate and/or MB dose (e.g., from an inappropriately high CIR value). In other examples, excessive DS's to account for low blood glucose concentrations might stem from inappropriately high basal rate and/or MB dose (e.g., from an inappropriately low CIR value).

SUMMARY

Devices, systems and methods are provided for maintaining glycemic control by adjusting, correcting and/or modifying fluid delivery based on fluid (e.g., insulin) delivery history. In some embodiments, features or mechanisms of adjusting, correcting and/or modifying the fluid delivery may be referred to as a "correction advisor." In some embodiments, the day may be divided into at least one time window. The at least one time window, according to some embodiments, may comprise at least one of a "pre-meal" and/or "post-meal" segment. The "pre-meal" segment may refer to a time window in which only basal doses are delivered to the patient. In some embodiments, for a pre-meal segment, a qualitative recommendation (e.g., a decrease or increase in the basal rate or delivery profile) can be implemented. For example, if a user typically administers a pre-meal CB dose to decrease a high blood glucose concentration, a recommendation or suggestion to increase the basal delivery profile may be provided. In some embodiments, the basal delivery profile may be quantitatively assessed based on a user's input regarding basal delivery profile, CB dose and DS times. The "post-meal" segment may refer to a time window which includes delivery of MB doses. In some embodiments, for a post-meal segment, a qualitative recommendation (e.g., a decrease or increase in the CIR value) can be implemented. For example, if a user typically administers a post-meal CB dose to decrease a high blood glucose concentration, a recommendation or suggestion to decrease the CIR may be provided.

Some embodiments of the present disclosure may be directed to methods for determining a parameter of a fluid delivery program for a therapeutic fluid delivery system. In some embodiments, the method may include providing a drug delivery system having a processor with instructions operating thereon to enable and/or perform retrieving data from a memory, the data corresponding to one or more time windows, assessing a correction delivery for the one or more time windows based on the data, determining a new CIR value for the one or more time windows if the correction delivery regularly follows a meal bolus and/or determining a new basal delivery profile for the one or more time windows if the correction delivery regularly precedes a meal bolus.

Some method embodiments may involve determining a parameter of a fluid delivery program for a therapeutic fluid delivery system by obtaining a first amount of fluid (e.g., insulin) delivered via correction boluses, obtaining a second amount of fluid (e.g., insulin) not delivered due to delivery suspension, assessing a difference between the first amount and second amount of fluid, and determining at least one parameter of the fluid (e.g., insulin) delivery program based on the subtraction of the second amount of fluid from the first amount of fluid. In some embodiments, assessing the difference may include subtracting the second amount of fluid from the first amount of fluid. The method may also include modifying the at least one parameter.

Some embodiments may further be directed to methods for adjusting therapeutic fluid delivery based on user parameters that include selecting one or more time windows, retrieving historical data relating to one or more past fluid delivery parameters of the user corresponding with the one or more time windows, processing the retrieved historical data, validating the processed historical data against one or more known parameters and adjusting the fluid delivery to the user based on some or all of the processed and valid historical data.

In some embodiments, methods for modifying drug delivery to a user are provided. Some embodiments may include receiving at least one or more time windows, retrieving historical data relating to one or more past drug delivery parameters of the user corresponding with the one or more time windows, determining one or more revised drug delivery parameters based on the historical data and modifying drug delivery to the user based on the determination upon the one or more revised drug deliver parameters if such one or more drug delivery parameters are valid.

In some embodiments, the historical data may include at least one of a correction bolus, a meal bolus and/or a basal suspension.

Some embodiments may further include averaging at least a portion of the historical data.

Some embodiments may include modifying one of a basal delivery profile and/or a CIR value.

In some embodiments, at least one or more of the time windows may include a plurality of time segments.

Furthermore, some embodiments may further include validating the one or more revised drug delivery parameters and, in some embodiments, validating may include checking whether one or more of the one or more revised drug delivery parameters exceeds a threshold value.

Some method embodiments may be directed to authenticating a user's input for a drug delivery system. In some embodiments, such methods may include receiving one or more inputs from a user, where such inputs comprise at least one parameter of a drug delivery program. Some embodiments may involve comparing the one or more inputs with historical data of the at least one parameter to determine whether the one or more inputs are valid. Some embodiments may involve notifying the user whether the one or more inputs are valid.

Methods according to the present disclosure may also be directed to adjusting therapeutic fluid delivery to a body of a user by obtaining at least one known personal parameters of a user and determining a modification to one or more delivery program parameters based on the at least one known personal parameters. Some embodiments may involve recommending an appropriate fluid dose based on the determined modification to the one or more delivery program parameters.

In some embodiments, obtaining the at least one known personal parameters of a user includes at least one of receiving the at least one known personal parameters from a user interface and retrieving the at least one known personal parameters from a memory.

Embodiments of the methods may include any of the features described in the present disclosure, including without limitation any one or more of the methods and systems, as well as any one or more of the above and/or the following features.

According to some embodiments of the present disclosure, methods for adjusting therapeutic fluid delivery based on known user parameters may include providing a fluid delivery device having a processor with instructions operating thereon for deriving delivery parameters based on one or more personal parameters of a user and a display for presenting a recommendation for an appropriate fluid dose in accordance with the derived delivery parameters. Some embodiments may include deriving one or more delivery parameters from one or more personal parameters of a user and determining an appropriate amount of fluid to deliver based on the one or more delivery parameters. Some embodiments may involve delivering the determined appropriate amount of fluid to the user.

Some embodiments may further comprise determining a bolus amount based on the derived one or more delivery parameters and/or determining a basal amount based on the derived one or more delivery parameters.

Moreover, in some embodiments, the one or more delivery parameters may be derived from a database that includes the one or more delivery parameters and corresponding personal parameters and/or the one or more delivery parameters may be derived from a mathematical function that correlates the one or more delivery parameters and the one or more personal parameters.

Embodiments of the methods may include any of the features described in the present disclosure, including without limitation any one or more of the methods and systems, as well as any one or more of the above and/or following features.

Embodiments of the present disclosure may also be directed to fluid delivery systems for determining a parameter of a fluid delivery program. System embodiments may include a dispensing unit configured to deliver a fluid from a reservoir into the body of a user and a processor having instructions operating thereon for retrieving data corresponding to one or more time windows from a memory, and assessing a correction delivery for the one or more time windows based on the data.

In some embodiments, the processor may also include instructions operating thereon for determining a new CIR value for the one or more time windows if the correction delivery regularly follows a meal bolus and/or determining a new basal delivery profile for the one or more time windows if the correction delivery regularly precedes a meal bolus.

In some embodiments, the data may include a first amount of fluid delivered via one or more correction boluses and a second amount of fluid not delivered due to one or more delivery suspensions. Some embodiments may also include assessing the correction delivery based on, at least in part, a difference between the first amount and second amount of fluid. Some embodiments may also include assessing the correction delivery by subtracting the second amount of fluid from the first amount of fluid.

Assessing the correction delivery may further include averaging the correction delivery of at least two time windows of the one or more time windows, each of the at least two time windows corresponding to the same time period on a different day, according to some embodiments.

In some embodiments, assessing the correction delivery may also include calculating a standard deviation of the averaged correction delivery and determining whether the standard deviation is smaller than a predetermined amount of fluid and/or whether the averaged correction delivery exceeds a predetermined amount of fluid. In some embodiments, the predetermined amount of fluid may be represented as a threshold value. In other embodiments, the predetermined amount may be represented as range boundaries.

In some embodiments, the processor may operate in a closed loop mode or a semi-closed loop mode. In some embodiments, the closed loop mode may include adjusting the CIR value and/or basal delivery profile upon determining the new CIR value and/or the new basal delivery profile. In some embodiments, the semi-closed loop mode may include recommending to the user via a user interface to adjust the CIR value and/or the basal delivery profile upon determining the new CIR value and/or the new basal delivery profile.

Some embodiments may comprise a notifier to notify the user about the determination of the new CIR value and/or new basal delivery profile, wherein the notifier may be selected from the group consisting of: a display, an audio alarm, a vibrating device and a light-emitting member.

In some embodiments, the new basal delivery profile may precede the one or more time windows for which the correction delivery was assessed to compensate for a lag period between a change in delivery rate and pharmacological effect.

The fluid delivered to the body, according to some embodiments comprises insulin.

In some embodiments, determining a modification of the new CIR value and/or new basal delivery profile may be based on influencing scenarios.

In some embodiments, the systems may further comprise a user interface configured to enable inputting at least one of the one or more correction boluses and the one or more delivery suspensions.

In some embodiments, the processor may have instructions operating thereon to enable and/or perform validating the correction delivery.

In some embodiments, when the correction delivery regularly follows a meal bolus, then if a value representative of the result of subtracting the second amount of fluid from the first amount of fluid is higher than zero, then the determined new CIR value may be lower than a programmed CIR value.

In some embodiments, when the correction delivery regularly follows a meal bolus, then if a value representative of the result of subtracting the second amount of fluid from the first amount of fluid is lower than zero, then the determined new CIR value may be higher than a programmed CIR value.

In some embodiments, when the correction delivery regularly precedes a meal bolus, then if a value representative of the result of subtracting the second amount of fluid from the first amount of fluid is higher than zero, then the determined new basal delivery profile may be higher than a programmed basal delivery profile.

In some embodiments, when the correction delivery regularly precedes a meal bolus, then if a value representative of the result of subtracting the second amount of fluid from the first amount of fluid is lower than zero, then the determined new basal delivery profile may be lower than a programmed basal delivery profile.

In some embodiments, the value representative of the result of subtracting the second amount of fluid from the first amount of fluid may be computed based on an average of the subtraction.

In some embodiments, the processor may have instructions operating thereon to enable and/or perform storing the new CIR value and/or new basal delivery profile in a memory.

In some embodiments, the processor may further have instructions operating thereon to enable and/or perform initiating delivery of fluid in correspondence with the new CIR value and/or new basal delivery profile.

Embodiments of the systems may include any of the features described in the present disclosure, including any of the features described above in relation to the methods as well as any one or more of the above and/or following features.

Some system embodiments of the present disclosure may be configured for adjusting therapeutic fluid delivered to a body of a user. In some embodiments, the system may include a dispensing unit configured to deliver the fluid from a reservoir into the body of the user and a user interface for inputting one or more parameters relating to, for example, correction boluses and/or delivery suspensions. The system may also include a memory configured to store the one or more parameters and a processor having instructions operating thereon for retrieving from the memory the one or more parameters and determining a modification of the fluid delivery amount based on at least one of these parameters, according to some embodiments. Determining the modification, in some embodiments, may include obtaining a first amount of fluid delivered by the one or more correction boluses, obtaining a second amount of fluid not delivered due to the one or more delivery suspensions and subtracting the second amount of fluid from the first amount of fluid.

Embodiments of the system may include any of the features described in the present disclosure, including any of the features described above in relation to the methods and/or other systems as well as any one or more of the above and/or following features.

In some embodiments, the system of the present disclosure may be directed to delivering therapeutic fluid to a body of a user based on user parameters and include a dispensing unit configured to deliver the fluid from a reservoir into the body of the user and a user interface for inputting one or more user parameters corresponding to at least one of the delivery programs, influencing scenarios, user interventions and body analyte data. System embodiments may also include a memory for storing the one or more user parameters and a correction advisor for retrieving from the memory or receiving from the user interface the one or more parameters of the user and determining a modification of at least one delivery program parameter based on at least one of the one or more parameters.

In some embodiments, determining the modification of the at least one delivery program parameter may be based on the one or more user interventions stored in the memory. In some embodiments, the one or more user interventions may include at least one of a meal bolus, correction bolus and/or delivery suspension. The modification of the at least one delivery program parameter may include changing at least one of a basal delivery profile or CIR value.

Furthermore, determining the modification of the at least one delivery program may be based on at least one health-related personal parameter, according to some embodiments. Some embodiments may also comprise modifying a bolus dose to be delivered to the user.

The system, according to some embodiments, may be configured to automatically adjust at least one delivery program parameter to provide a dynamic and customized delivery program to a user.

Embodiments of the system may include any of the features described in the present disclosure, including any of the features described above in relation to the methods and/or other systems as well as any one or more of the above and/or following features.

In some embodiments, fluid delivery systems of the present disclosure may include an fluid (e.g., insulin) dispensing unit, a user interface configured for inputting one or more personal parameters of the user, a processor having instructions operating thereon to derive one or more fluid delivery parameters based on the one or more personal parameters of the user and a display presenting a recommendation for an appropriate fluid dose in accordance with the derived one or more fluid delivery parameters.

In some embodiments, the derived one or more fluid delivery parameters may include parameters selected from the group consisting of a total daily dose of insulin, total basal dose of insulin, carbohydrate-to-insulin ratio and insulin sensitivity. In some embodiments, one or more personal parameters including parameters selected from the group consisting of body weight, Body Mass Index, fat percentage, waist circumference, heart rate, blood pressure and maximal oxygen consumption.

Embodiments of the system may include any of the features described in the present disclosure, including any of the features described above in relation to the methods and/or other systems as well as any one or more of the above and/or following features.

Embodiments of the present disclosure may also be directed to drug delivery systems for administering a therapeutic fluid to a body of a user. In some embodiments, the system may include a processor having means for deriving one or more delivery parameters based on one or more personal parameters of the user and a pump for dispensing the therapeutic fluid from a reservoir into the body of the user. In some embodiments, the means for deriving the one or more delivery parameters may operate used in conjunction with the processor to control the pump for dispensing the therapeutic fluid based on the one or more delivery parameters.

Embodiments of the system may include any of the features described in the present disclosure, including any of the features described above in relation to the methods and/or other systems.

In some embodiments, the CIR value can be quantitatively assessed based on the user's input of TC, MB dose, CB dose and DS times. The amount of delivered CB doses and delivery suspensions may be summed for each time window, daily. If a CB dose is larger or smaller than a delivery dose that was not administered during DS periods, the difference may indicate the occurrence of an under- or over-delivered amount of fluid, respectively. Avoiding the repetition of these occurrences may be done by either adjusting the basal rates or the CIR value.

In some embodiments, an average of the summed amount of delivered CB doses and DS's for each time window over a period of time (e.g., a week) may be calculated. The basal rate and/or the CIR value can be adjusted according to the averaged sum of CB doses and DS's. In some embodiments, an over- or under-delivery dose which regularly occurs in the pre-meal segment may suggest that an adjustment of the basal delivery profile for the time window is required. An over- or under-delivery dose which regularly occurs in the post-meal segment may suggest that an adjustment of the CIR value for the time window is required.

In some embodiments, the basal dose and/or the CIR value may be adjusted if the average sum of CB doses and DS's is greater or less than a required amount (i.e., a threshold) of fluid.

Some embodiments of the present disclosure are directed to a drug delivery system. The system may include a user interface configured for receiving a desired change in insulin delivery (e.g., the CB dose or DS), a memory configured to store data (e.g., basal rates, MB dosages and schedule, CB dosages and schedule, number and timing of DS's), a real time clock, a processor/controller (e.g., a CPU) configured to adjust the basal rate and/or CIR value for example, based on data stored in memory.

In some embodiments, the system may include a screen or display for providing a graphical representation (e.g., a visual indication) of the adjusted basal rate and/or CIR value to a user. In some embodiments, the system may be a remotely-controlled skin securable insulin pump.

In some embodiments, a programmed dose may relate to a drug delivery dosage (e.g., a basal and/or bolus dose) corresponding to drug delivery parameters stored in memory. A correction delivery (e.g., the over- or under-delivered amount of insulin) may correspond to the sum of CB doses and DS periods. A modified delivery profile relates to the delivery program resulting from the correction advisor, according to some embodiments. In some embodiments, a dose may relate to a value, a range of values or a delivery profile of an amount of therapeutic fluid delivered to the body.

In some embodiments, for a post meal segment, a qualitative recommendation (e.g., decrease or increase the CIR value) can be implemented. For example, if a user typically administers a post-meal correction bolus in order to decrease a high BG level, a recommendation/suggestion to decrease the CIR may be performed.

In some embodiments, the CIR value can be quantitatively assessed based on the user's input of carbohydrate load (TC), the MB doses, CB doses and DS times.

In some embodiments, a new CIR value recommendation can be provided to the user. This value should be accurate when the amount of consumed carbohydrates is known. In some embodiments, the basal rate and/or CIR value can be modified if the total over- or under-delivered amount of insulin exceeds a certain threshold value, for example, a percentage (e.g., 20%) of the user's TDD or a percentage value of the total segmental dose of insulin during a given time period. In some embodiments, the threshold value can be set by the user or a caregiver (e.g., a parent, physician or certified diabetes educators (CDE)).

In some embodiments, the over- or under-delivered amount of insulin may be averaged over a certain time period (e.g., 4-20 days) and the basal rate and/or CIR modifications may be assessed accordingly. In some embodiments, the basal rate and/or CIR may be modified if the standard deviation (SD) of the average over- or under-delivered amount of insulin does not exceed a pre-defined threshold.

In some embodiments, the command to adjust, correct or modify the basal delivery rate may precede the time window relating to the over- or under-delivery by an amount of time (e.g., 30-60 minutes) sufficient to compensate for the lag period between the change in insulin delivery rate and pharmacological effect (for example due to the delay of insulin absorption from the subcutaneous tissue).

Some embodiments of the system may also include an analyte sensing device (e.g., glucometer). The system may further include a remote control unit. In some embodiments, the sensing device may be located in the remote control unit, in a dispensing unit of the system or both. In some embodiments, the system may include a continuous glucose monitor (CGM). In some embodiments, the CGM may be located in a dispensing unit of the system.

In some embodiments, operation of the system may be carried out manually by operating buttons and/or switches located on the dispensing unit. In some embodiments, the dispensing unit may have a disposable part and a reusable part. The disposable part can include a reservoir, outlet port and other relatively inexpensive components. The reusable part can include electronics (e.g., a printed circuit board and/or a processor), at least a portion of the driving mechanism and other relatively expensive components (e.g., sensors).

In some embodiments, a cradle unit can be provided with the system. The cradle unit can be a substantially flat sheet that adheres to the skin and enables disconnection and reconnection of the dispensing unit from and to the patient's skin upon patient discretion. After attachment/adherence of the cradle unit to the skin, a cannula for insulin delivery may be inserted into the subcutaneous compartment of the patient through a dedicated passageway located in the cradle unit.

Some embodiments of the present disclosure may be directed to devices, systems and methods configured to provide accurate quantification of insulin doses according to user-specific diabetes variables that are based on known personal parameters. In some embodiments, insulin dosage may be derived from at least one delivery program parameters (also referred to as a user-specific variable or USV), including without limitation TDD, TBD, CIR and IS. These parameters may be derived from at least one personal parameter (also referred to as a user-known parameter or UKP), including without limitation body weight, BMI, fat percentage, waist circumference, heart rate, blood pressure, and maximal oxygen consumption ($VO_2$ max). Some embodiments may include a processor and a memory that stores at least one derived parameter. Some device embodiments may include a glucose monitor (e.g., glucometer) and/or a CGM. Some device embodiments may include a remotely-controlled, skin adherable dispensing unit having a reusable part and a disposable part.

DETAILED DESCRIPTION

The present disclosure generally relates to devices, systems, methods and features for adjusting fluid delivery (e.g., insulin delivery) based, at least in part, on past or historical fluid delivery data and/or personal parameters of a user (also referred to as "patient"). In some embodiments, historical fluid delivery data and/or personal parameters may be used to adjust, modify or otherwise control basal rates, delivery profiles or patterns and/or CIR values. The mechanism or feature of adjusting fluid delivery program parameters, such as modifying basal rates, bolus doses and/or CIR values based on historical data and/or personal parameters may be referred to as the "correction advisor." To this end, in some embodiments, the correction advisor may be configured to operate within a fluid dispensing system. In some embodiments, the correction advisor may be implemented in a fluid dispensing unit and, in particular, in a portable therapeutic fluid infusion pump. The terms "dispensing," "delivery" and "infusion" are used herein interchangeably to generally refer to the administration or distribution of a substance into the body.

Some embodiments of the present disclosure may include a fluid delivery system having a fluid dispensing unit which may include a reusable part and a disposable part. The system may further include a remote control. In some embodiments, the reusable part may contain relatively expensive components, such as electronics, at least a portion of a driving mechanism, sensors, motors and various other components. Some embodiments of the disposable part may include less expensive components, such as a reservoir for containing therapeutic fluid (e.g., insulin), a connecting tube for delivering therapeutic fluid, and a piston and/or plunger assembly for pumping fluid from the reservoir into the body. Other pumping mechanisms such as peristaltic, piezoelectric, and the like may be used. A power supply (e.g., one or more batteries) for providing power to at least one of the reusable and/or disposable parts of the fluid dispensing unit may be located in the disposable part, the reusable part, or shared therebetween. The power supply may be rechargeable or non-rechargeable. In some embodiments, the disposable part may also be configured with a portion of the driving mechanism, such that the driving mechanism would be shared, under those circumstances, by both parts (the disposable and the reusable).

Figure 1A:
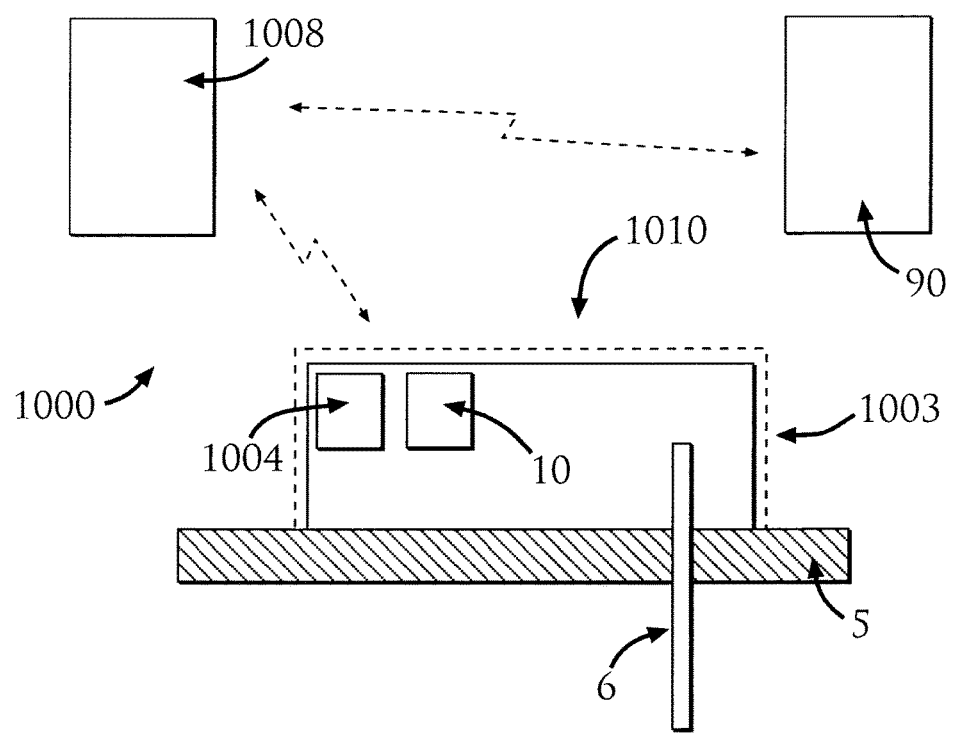
FIGS. 1a-1c illustrate a fluid delivery system including a dispensing unit and a remote control unit, according to some embodiments of the present disclosure.
Figure 1B:
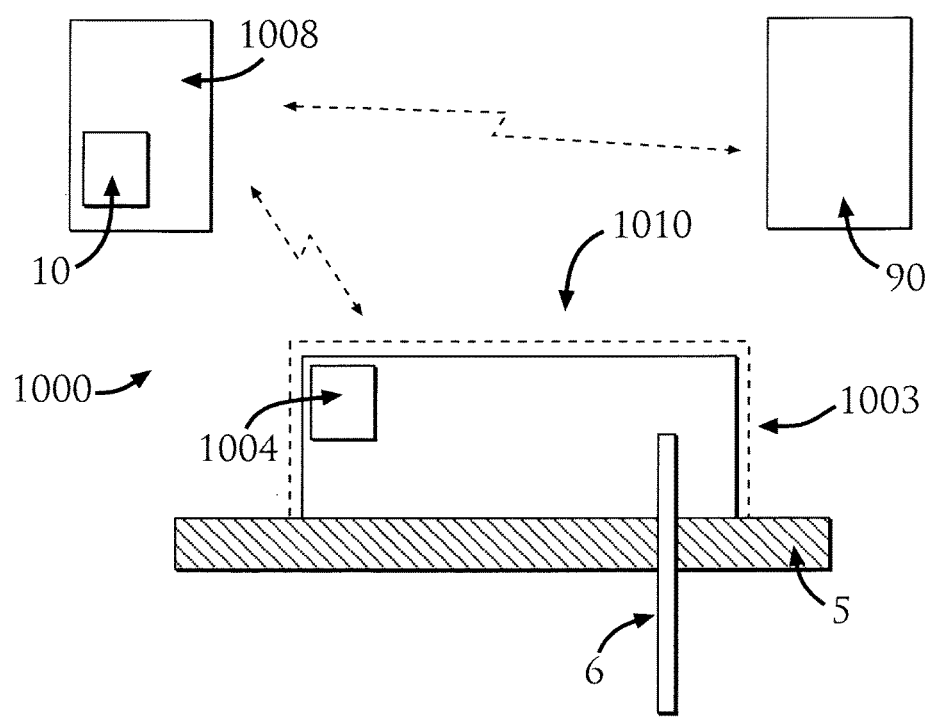
Figure 1C:
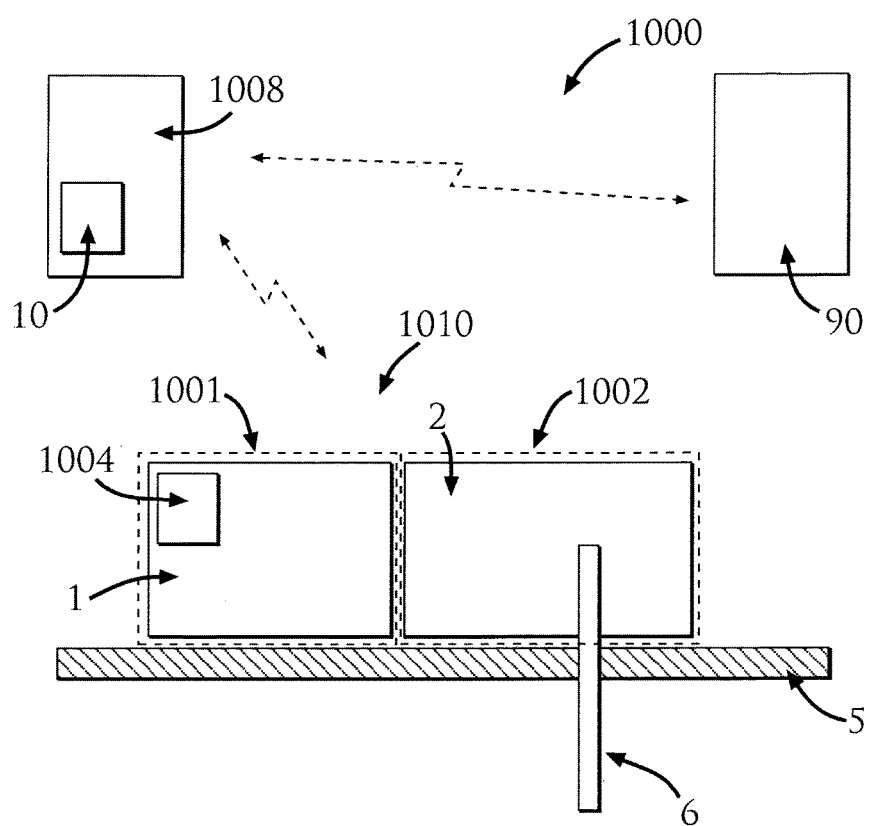

FIGS. 1a-1c show a fluid delivery system 1000 for dispensing therapeutic fluids (e.g., insulin) into the body of a patient according to some embodiments of the present disclosure. Some embodiments of the system 1000 may include a dispensing unit 1010 having a dispensing mechanism. (e.g., syringe with a propelling piston, peristaltic). The system 1000 can include a remote control unit 1008 and in some embodiments, can further include a glucose monitor (e.g., blood glucose monitor ("BGM")) 90. The dispensing unit 1010 may be connected to a cannula 6 that penetrates a patient's skin 5 to deliver therapeutic fluid (e.g., insulin) into the body (e.g., subcutaneous tissue). The dispensing unit 1010 may be a single component having one housing 1003 (as illustrated in FIGS. 1a and 1b) or a two-part component having housings 1001 and 1002 as illustrated in FIG. 1c. In some embodiments, housing 1001 (or part 1) may be reusable and housing 1002 (or part 2) may be disposable.

In some embodiments, flow programming and data acquisition can be done using a remote control unit 1008 or using one or more operating buttons and/or switches 1004 located on the dispensing unit 1010 (e.g., on the unit's housing). Some embodiments of the system 1000 may include at least one processor or controller, at least one memory, at least one input means (e.g., a keypad, keys, buttons, switches, touchscreen or audio/voice commander), at least one screen or display and at least one notification means. The notification means may include without limitation audible means (e.g., buzzer) or vibrational means (e.g., vibrator). Each of the foregoing components may reside in the remote control unit 1008, the dispensing unit 1010 or both. Embodiments of the remote control unit 1008 may be implemented, for example, in one of a Personal Data Assistance (PDA), a cellular phone, a watch, a media player (e.g., an iPod, iPad), a smartphone (e.g., an iPhone or Android device), a laptop and/or a PC. Example embodiments of system 1000 are disclosed in U.S. Patent Application Publication No. 2007/0106218 and International Publication No. WO 2009/125398, the disclosures of which are incorporated herein by reference in their entireties. In some embodiments, the system 1000 may include at least one of a BGM or continuous glucose monitor ("CGM"). The glucose monitor may be contained within the remote control unit 1008, dispensing unit 1010 or a separate unit preferably configured to establish one- or two-way communication (e.g., wireless, RF, IR, induction) with the dispensing unit 1010 or remote control unit 1008. In some embodiments, the glucose monitor may be shared between a plurality of units/part/components of the system. In some embodiments, a CGM contained within the dispensing unit 1010 may be positioned within a reusable part of the unit 1010, a disposable part of the unit 1010 or both. Some embodiments may include a sensing element (e.g., an electrochemical sensor or electrodes) disposed on the cannula 6. Example embodiments are disclosed in U.S. Patent Application Publication Nos. 2007/0191702 and 2008/0214916), as well as International Publication No. WO 2009/066288, the disclosures of which are incorporated herein by reference in their entireties. In some embodiments, the correction advisor 10 may be located in the dispensing unit 1010 (see FIG. 1*a*), in the remote control unit 1008 (see FIGS. 1*b* and 1*c*) or shared between the two units (1010 and 1008). In some embodiments, the correction advisor may be implemented in another component of the system, such as a PC.

Figure 2:
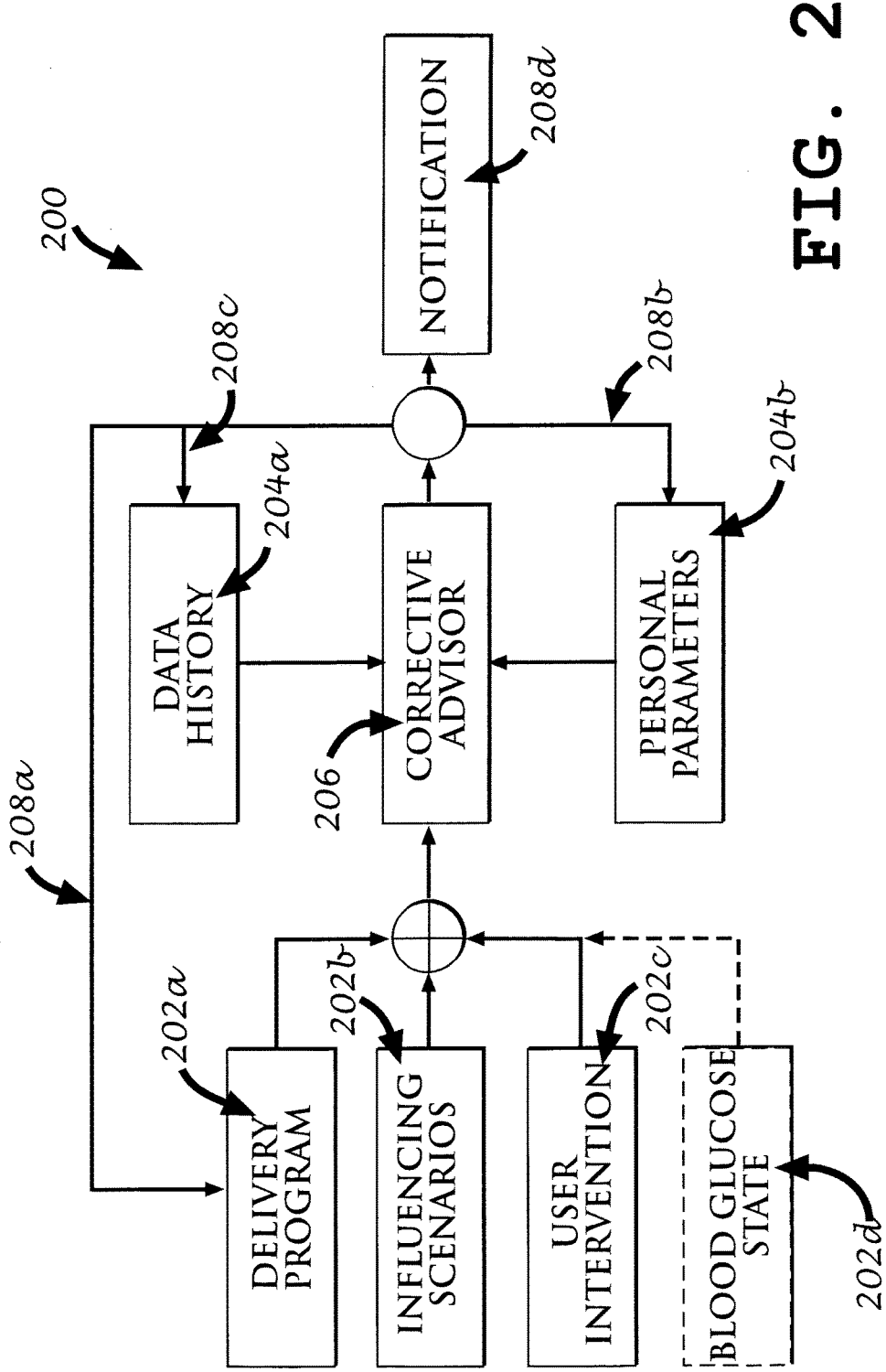
FIG. 2 illustrates a flow diagram depicting a system capable of adjusting, correcting or modifying the delivery of a fluid, according to some embodiments of the present disclosure.

FIG. 2 depicts a system 200 configured to adjust, correct and/or modify therapeutic fluid delivery (e.g., insulin delivery). The correction advisor 206 (also designated as 10 in FIGS. 1*a*-1*c*) may receive various inputs. In some embodiments, a delivery program 202*a* may provide the correction advisor 206 with various parameters, including without limitation, prospective, projected or planned delivery profiles, patterns, dosages and other fluid delivery characteristics. In some embodiments, the delivery program 202*a* may provide parameters that include without limitation programmed basal delivery profiles, bolus dose preferences programmed (e.g., by the user and/or caregiver), and other diabetes-related parameters, such as TBG, IS, CIR, insulin type (e.g., rapid-acting insulin or regular insulin), site of cannula insertion, duration of insulin activity ("DIA"), RI (also referred to as "Bolus On Board"), insulin absorption characteristics (e.g., the rate) and TDD. In some embodiments, the delivery program 202*a* may be stored in a memory by the correction advisor 206 (for example) and executed by at least one processor (e.g., CPU, MCU). In some embodiments, the processor may comprise the correction advisor 206 or the correction advisor 206 may operate thereon. The memory, correction advisor 206 and/or processor may be located in the dispensing unit 1010, remote control unit 1008 or both, or in other components of the system. In some embodiments, the parameters programmed into the delivery program 202*a* may be set or modified by the user, a caregiver and/or by the correction advisor 206. The modified parameters may be stored in data history 204*a*, shown in FIG. 2 as reference numeral 208*c*, and/or in personal parameters 204*b*, shown in FIG. 2 as reference numeral 208*b*, for future use.

In some embodiments, the correction advisor 206 may receive one or more influencing scenarios 202*b*, which may include without limitation data related to carbohydrate intake (e.g., time of intake, amount of carbohydrates consumed, description of the intake, glycemic index, glycemic load, amount of fibers, fat content, prevalence of intake, or the ingredients of the food or drink consumed). Data related to carbohydrate intake may be stored in memory and/or be associated with a food database, for example, by the correction advisor 206. In some embodiments, the influencing scenarios 202*b* may include without limitation physical activity (e.g., sports or sleeping) and other personal parameters of the user. Some embodiments of the present disclosure may refer to personal parameters that are characteristic of a patient's general physical state. Such personal parameters may include without limitation age, gender, body temperature, body weight, Body Mass Index ("BMI"), fat percentage, waist circumference, heart rate, blood pressure or maximal oxygen consumption (i.e., "$VO_2$ max"). Data related to influencing scenarios 202*b* may be stored in data history 204*a*, shown in FIG. 2 as reference numeral 208*c*, and/or in personal parameters 204*b*, shown in FIG. 2 as reference numeral 208*b*, for future use.

In some embodiments, the correction advisor 206 may receive one or more user interventions 202*c*, including but not limited to input relating to bolus administration (e.g., the time, dosage and/or type), basal delivery profile change(s) and/or DS. Data related to user interventions 202*c* may be stored in data history 204*a*, shown in FIG. 2 as reference numeral 208*c*, and/or in personal parameters 204*b*, shown in FIG. 2 as reference numeral 208*b*, for future use.

In some embodiments, the correction advisor 206 may receive data 202*d* related to a body analyte, such as for example glucose concentration or glucose concentration trends. Data 202*d* may be provided, according to some embodiments, by a CGM or any other suitable glucometer or glucose monitor. In some embodiments, glucose concentrations may be measured in the blood, interstitial fluid ("ISF") or in other tissues or compartments of the user's body. The measured glucose concentration will typically correspond to the blood glucose concentration and a correlation may be carried out. Data 202*d* related to the body analyte may be stored in data history 204*a*, shown in FIG. 2 as reference numeral 208*c*, and/or in personal parameters 204*b*, shown in FIG. 2 as reference numeral 208*b*, for future use.

Some embodiments of the correction advisor 206 may be configured to retrieve past or historical fluid delivery data, indicated in FIG. 2 as data history 204*a*, from a memory. The data history 204*a* may include information collected during a patient's usage of the fluid delivery system 1000 and stored in memory. In some embodiments, the data history 204*a* may include past records of one or more inputs relating to the parameters of delivery program 202*a*, influencing scenarios 202*b*, user interventions 202*c* or body analyte data 202*d*. In some embodiments, the data history 204*a* may be implemented as logbooks and/or schedules. The correction advisor 206 may receive and/or retrieve at least some of the data from the data history 204*a*, process it (and/or correlate it), store it in memory and/or use it for further purposes. In some embodiments, for example, the correction advisor 206 may use data from the data history 204*a* to compute (i) the average of basal rate for every Tuesday during the last year, (ii) the average total insulin delivery between 2 pm and 8 pm during the last week, (iii) the trend over the past year in carbohydrates estimation and correlation between this estimation and the area under the curve of corresponding glucose level and/or (iv) the variation in bolus administrations after lunch during the last week. In some embodiments the correction advisor 206 may analyze one or more inputs relating to the parameters of delivery program 202*a*, influencing scenarios 202*b*, user interventions 202*c* or data 202*d* using data retrieved from the data history 204*a*.

In some embodiments, the correction advisor 206 may receive via a user interface and/or retrieve from a memory, data relating to personal parameters 204*b* regarding the physical state of the patient, as shown in FIG. 2. The personal parameters 204*b* may include without limitation data relating to general physical state and/or well-being of the user, such as physical activity levels, body temperature, weight, age, gender, heart rate, blood pressure and any other health-related parameters of the user. In some embodiments, the correction advisor 206 may use at least one of the personal parameters 204*b* to derive at least one delivery program 202*a* parameter (e.g., TBG, TDD or IS). The derived parameter may affect the amount of fluid delivered via a bolus dose, for example.

In some embodiments, the correction advisor 206 may receive or retrieve one or more of inputs relating to the parameters of delivery program 202*a*, influencing scenarios 202*b*, user interventions 202*c* or body analyte data 202*d* and, based on further data received or retrieved from the data history 204*a* and personal parameters 204*b*, may process, calculate or compute an adjustment, modification or correction in the current delivery program, as shown in FIG. 2 as reference numeral 208*a*. For example, based on average past or historical fluid delivery data (i.e., data history 204*a*), the correction advisor 206 may recommend to a user or instruct a processor to adjust the basal rate. In another example, based on past or historical fluid delivery data (i.e., data history 204a), the correction advisor 206 may recommend to a user or instruct a processor to adjust the CIR value in order to affect an MB. In yet another example, based on a personal parameter 204b, the correction advisor 206 may recommend to a user or instruct a processor to adjust at least one delivery program 202a parameter and to affect one or more bolus doses. In turn, the correction advisor 206 may then update the data history 204a, shown in FIG. 2 as reference numeral 208c, and/or update the personal parameters 204b, shown in FIG. 2 as reference numeral 208b, with such adjustment for future use of the modified delivery program 202a parameters.

In some embodiments, the correction advisor 206 may provide a notification 208d to the user via a suitable notification means (e.g., a graphic display, beeper, buzzer or vibrator) regarding data updates, any adjustments made by the correction advisor 206, any alarm or alert related to the correction advisor 206, and/or recommendations provided by the correction advisor 206. For example, in some embodiments, after concluding that the basal rate has to be adjusted, the correction advisor 206 may notify the user via a message on a screen located on remote control unit 1008 and/or dispensing unit 1010: "It is recommended that you adjust the basal rate to 2 U/hr." Then, the user may accept this recommendation or reject it via the user interface.

In some embodiments, correlations or computations carried out by the correction advisor 206 may be implemented via matching tables or matrices, mathematical correlations and/or calculations. In some embodiments, the data history 204a and/or personal parameters 204b may be a database stored in a memory which includes a mathematical expression, function or operator (e.g., analytic, numeric, empirical).

In some embodiments, the data history 204a and/or personal parameters 204b may be generated by the patient or caregiver using a user interface on the dispensing unit 1010 or remote control unit 1008. In some embodiments, the data history 204a and/or personal parameters 204b may be automatically recorded by a processor or controller or by the correction advisor 206. Alternatively, the delivery program 202a, influencing scenarios 202b, user interventions 202c or body analyte data 202d of the system 200 may include tables (e.g., schedules or look-up tables) that are receivable or downloadable from a remote source (e.g., wirelessly from the internet or a PC).

In some embodiments, the system 200 may be configured to tailor, adapt or customize fluid delivery program to a specific user. Mathematical behavior may be obtained by implementing curve-fitting of data specific to the patient (e.g., customizing). Deriving the user-specific behavior may be implemented in a self-learning system employing conventional techniques known to one skilled in the art, including without limitation linear or non-linear curve fitting, Bayesian models, neural network, fuzzy logic or genetic algorithms. Performance of the system 200 may enable dynamic adjustment of insulin delivery for each user to provide for improved diabetic care based on the data history 204a and/or the personal parameters 204b, for example.

In some embodiments, the system 200 may operate in a closed-loop mode (i.e., automatic feedback with no need of user interference), or in a semi-closed loop mode (i.e., requiring user interference in confirming part of the instructions).

In some embodiments, the system 200, and in particular the correction advisor 206, may function as a safety means to prevent inaccurate or undesirable inputs of the user. In other words, the system 200 may serve as a validation system to validate the reliability and/or credibility of user's input. For example, if a user instructs the fluid delivery system to administer a bolus dose of 122 U, the correction advisor 206 can compare and/or correlate this dose with an average of past bolus doses administered by the user (i.e., data history), and determine and/or recommend to the user that the dose of 122 U exceeds that user's "normal range" of a bolus dose, typically used by the user. An inaccurate input may occur, for example, if the user would like to enter "12 U" but inadvertently presses the '2' key twice and enters "22 U." This safety mechanism may prevent fatal errors. In some embodiments, the dispensing unit 1010 may include fixed boundaries for various ranges (e.g., a bolus may not exceed the range of 1 U and 20 U). Implementing the system 200 and correction advisor 206 may set dynamic boundaries, tailored or customized for each user.

In some embodiments, the data history may be stored in logbooks and/or databases which can be analyzed by diabetic professionals (e.g., CDEs or physicians) enabling monitoring of the user and improving his/her diabetic care.

Figure 3:
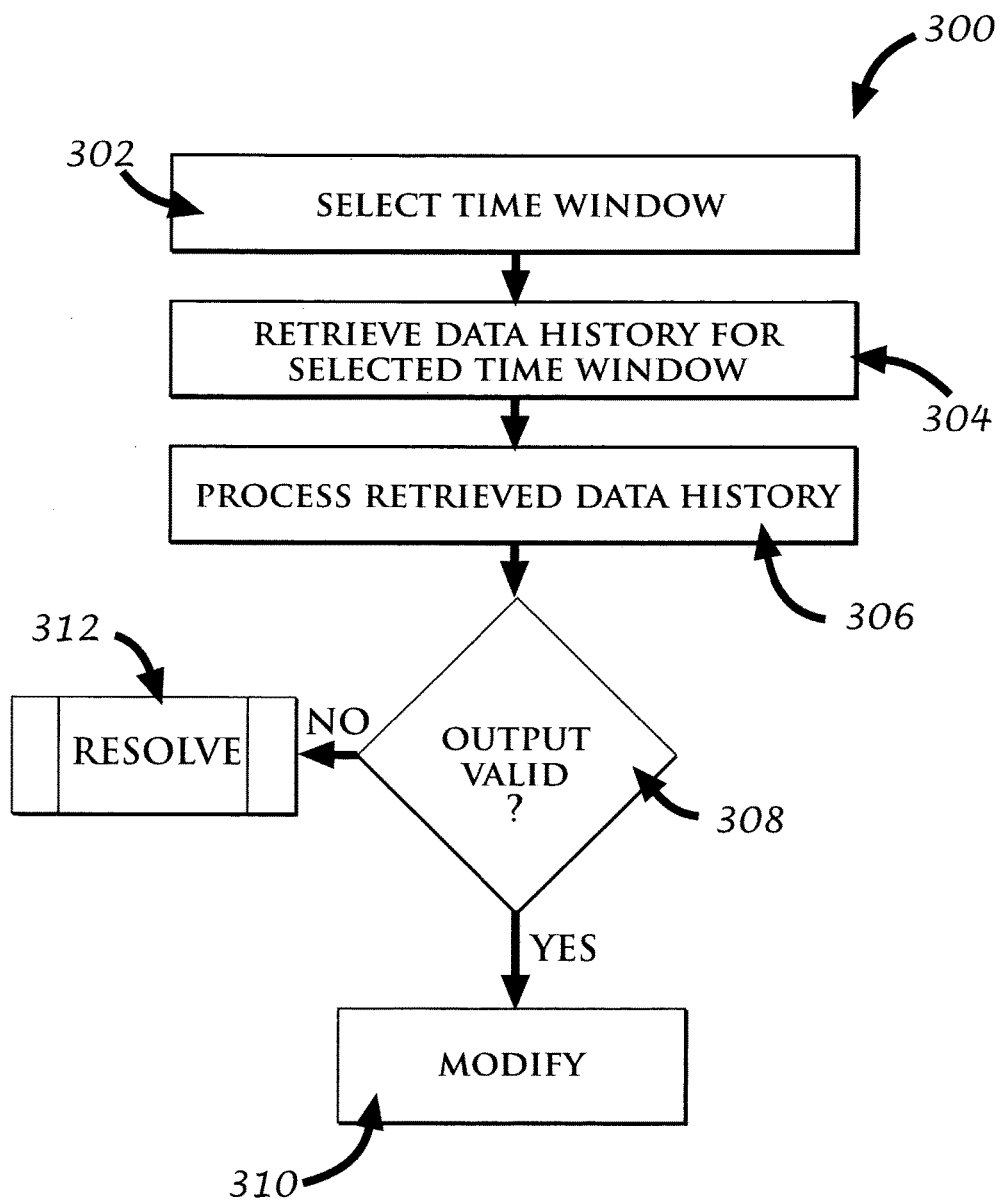
FIG. 3 illustrates a flow diagram depicting a procedure for adjusting, correcting or modifying fluid delivery based on data history, according to some embodiments of the present disclosure.

FIG. 3 is a flow diagram depicting a procedure 300 for adjusting, correcting and/or modifying fluid delivery based on data history (shown in FIG. 2 as reference numeral 204a) relating to the user. In some embodiments, a time window may be selected (e.g., between 3 pm and 5 pm on a specific day, or between 5 am and 10 am on the past eight Mondays), as shown in FIG. 3 at step 302. At step 304, some or all of the data history (shown in FIG. 2 as reference numeral 204a) corresponding to the selected time window may be retrieved. This data may consist of previous delivery programs, influencing scenarios, user interventions or body analyte data (shown in FIG. 2 as reference numerals 202a, 202b, 202c, and 202d, respectively). At step 306, the retrieved data may be processed. In some embodiments, processing may include averaging bolus administrations of the retrieved data and calculating a new basal rate therefrom. At step 308, the processed data (the "output") may be validated. In some embodiments, validation of the output may include checking whether the output is greater than or less than a predetermined threshold. In some embodiments, validation may include checking whether the standard deviation of an average bolus dose falls within pre-defined boundaries, e.g., ±24%. If the output (e.g., changing the basal rate to 2 U/hr or reduce basal rate in 30%) is valid, then the instruction can be executed 310, either automatically or upon confirmation by the user. If the output is invalid, then a resolve procedure, shown at step 312 in FIG. 3, may be performed.

Embodiments of the present disclosure may be configured so that the resolve procedure at step 312 automatically validates the inputs, informs the user that a failure has occurred, instructs the user to re-input some or all of the past data or, in some embodiments, directs the user on how to resolve the problem. In some embodiments, procedure 300 may be performed in a close-loop mode or in a semi-close loop mode. In some embodiments, procedure 300 may be performed for a plurality of time windows, for example in a single day. In some embodiments, a time window can be defined in terms of meal time, e.g., "pre-meal" to indicate that the time window occurs before a meal or "post-meal" to indicate that the time window occurs after a meal. In some embodiments, the time window may include both "pre-meal" and "post-meal" segments.

Figure 4:
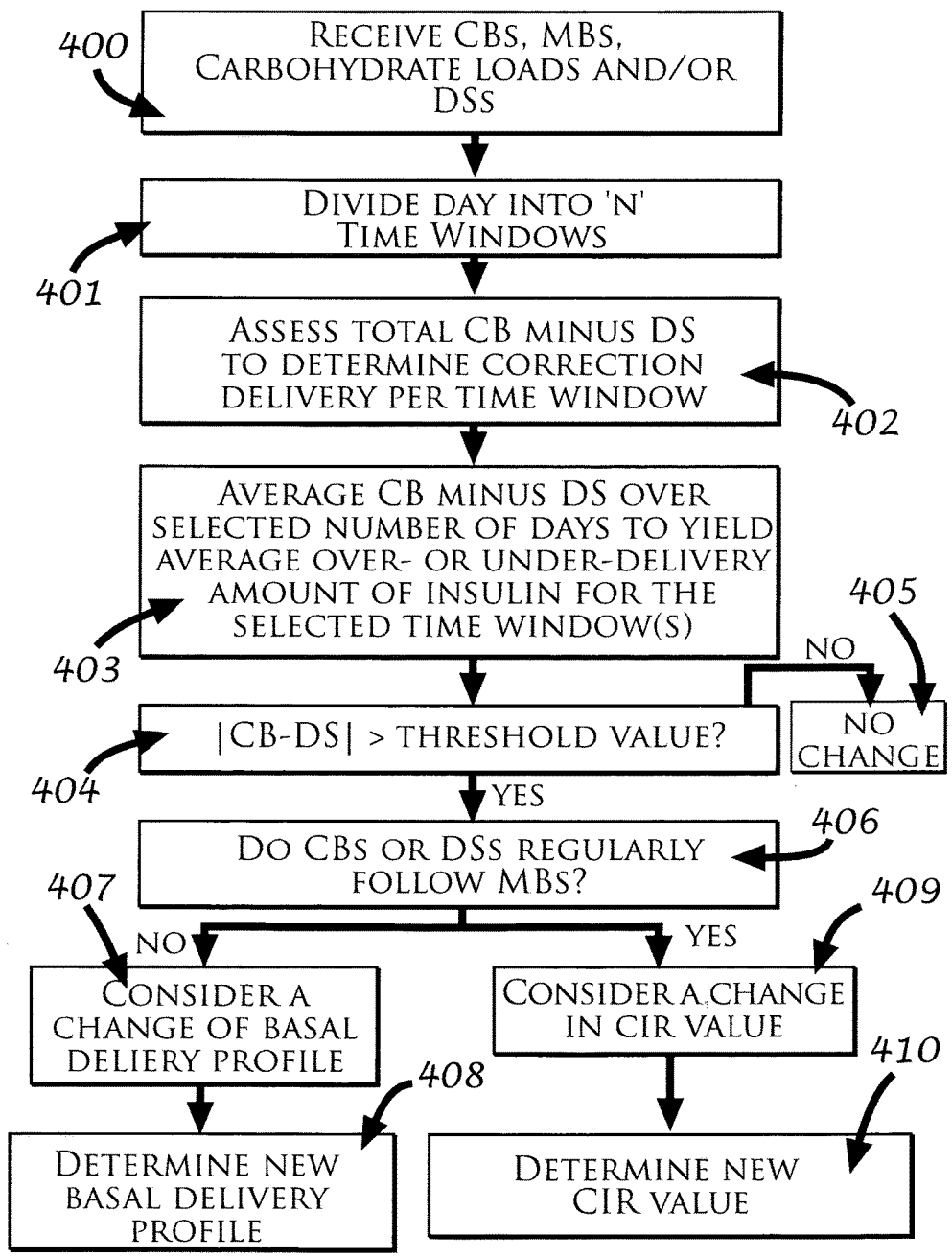
FIG. 4 illustrates a flow diagram of a procedure to adjust, correct or modify basal delivery profiles and/or CIR values, according to some embodiments of the present disclosure.

FIG. 4 illustrates a flow diagram of an example procedure for adjusting fluid delivery based on past or historical fluid delivery data. Adjusting insulin delivery based on past or historical fluid delivery data may be used to maintain TBG levels within a suitable range or value. In some embodiments, the historical data may include basal delivery profiles, rates or patterns and/or CIR values in accordance with previous fluid deliveries and/or suspensions. At step 400, MB and CB doses, DS's and/or TC amounts may be received from data 202*a*-*d* and/or data history (shown in FIG. 2 as reference numerals 202*a*-*d* and 204*a*, respectively). In some embodiments, these parameters may be inputted by the user and their amount and/or time can be stored in a memory. In some embodiments, a processor may record the time and/or amount of CB, MB, DS and/or carbohydrate load and store them in memory for later retrieval, for example, by the correction advisor 206. In some embodiments, the value of one or more of the parameters may be zero, for example if there are no DS, then DS is zero. At step 401, a day may be divided into multiple time windows. The number of time windows may be indexed and designated by a variable n, (e.g., n=3).

The time windows may be characterized in some embodiments in equal or different durations. For example, a first time window may be 01:00-03:00 (duration of 2 hours), a second time window may be 03:00-08:00 (duration of 5 hours) and a third time window may be 08:00-10:00 (duration of 2 hours). The variable n may be any integer equal to or greater than 1. In some embodiments, the time window may be derived according to meal times. For example, if the user defined the meal times as breakfast at 08:00, lunch at 13:00 and dinner at 19:00 and the post-meal duration as 4 hours, then the post-meal time windows (also referred to as "post-meal" segments) would be 08:00-12:00 (post-breakfast), 13:00-17:00 (post-lunch), and 19:00-23:00 (post-dinner). The pre-meal time windows (also referred to as "pre-meal" segments) may be: 12:00-13:00, 17:00-19:00 and 23:00-08:00 (day after).

In some embodiments, a meal may be characterized by more than one parameter. For example, a meal may have a single representative time, e.g., 08:00. In some embodiments, a meal may have a start time and an end time (e.g., 08:00, 08:30). In some embodiments, a meal may have a start time and duration (e.g., 08:00, 30 minutes). Accordingly, an average correction delivery in the post-meal time windows may be calculated based on, for example, a calculation of the average correction delivery of a four-hour time window after breakfast during last week.

As shown at step 402, the total amount of insulin delivered as a CB dose and the total amount of insulin that was not being delivered, i.e., suspended (DS) by the user, may be assessed per each time window. For example, if during a specific time window two CB doses of 3 U and 2 U were delivered and a basal delivery rate of 1 U/h was suspended for 30 minutes, then a gap would exist between the programmed (i.e., planned or projected) insulin delivery amount and the fluid amount actually delivered (considering the corrections in the form of CB doses and DSs). In this example, the gap (i.e., the under-delivered amount of insulin) would be 4.5 U (i.e., 2 U+3 U−1 U/hr*0.5 hr). Alternatively, if for a specific time window a CB dose of 1 U was delivered and a basal delivery rate of 2 U/h was suspended for one hour, then there would exist a gap between the programmed insulin delivery amount and the dose actually delivered of −1 U (i.e., 1 U−2 U/hr*1 hr). This would be the amount of insulin over-delivered to the patient during that particular time window.

A numerical example is given below for a pre-meal time window:
time window for "pre-meal" segment: 10:00-14:00 (total of 4 hours before meal)
programmed basal rate during the time window: 1 U/h
the dose of CB doses during this time segment: 3 U at 11:00 and 2 U at 13:00 resulting in a total of 5 U delivered
DS times during this time window: 12:00 to 13:00, for a total of 1 U not delivered (i.e., delivery in a 1 U/h basal rate)
summing the CB doses and DS's during the time window results in an under-delivered amount of insulin of 4 U (i.e., 5 U−1 U). This is the dosage amount that was missing during this time window. In other words, the user had to correct the programmed delivery by adding 4 U of insulin, in this particular time window. It can be delivered, for example, by temporarily adjusting the basal rate to 2 U/h during this time window. In some embodiments, the above calculation may be repeated during a time period (e.g., a week) and the amount of insulin under-delivered (or over-delivered) during the time window may be averaged. The average may then be used to recommend a new basal delivery profile.

A numerical example is given below for a post-meal time window:
time window for post-meal segment: 12:00-14:00 (total of 2 hours)
programmed CIR value: 10 g/U
total carbohydrates consumed during the meal: 160 g
total bolus dose delivered to cover the above carbohydrate intake: 16 U
CB doses delivered during the post-meal time window: 2 U (at 13:00)+2 U (at 14:00)=4 U
DS's during the post-meal time window: none
sum of the CB doses and the fluid amount corresponding to the DS times: 4 U
Thus, a total of 4 U should have been further administered during the time window. According to some embodiments, the under-delivery of insulin may be corrected by lowering the CIR value during the relevant post-meal time window to 8 g/U (i.e., 160 g/20 U). In some embodiments, the above calculation may be repeated during a period of time (e.g., a week) and the amount of insulin under-delivered (or over-delivered) during the time window may be averaged. The average may then be used to recommend a new CIR value.

As indicated at step 403, over- or under-delivered amounts of insulin for a select time window may be averaged over a period of time (e.g., 3-7 days). So, for example, if during a time window from 15:00-17:00 the over-delivered amount of insulin for three consecutive days was 3.8 U, 4 U and 4.2 U, respectively, then the average over-delivered amount of insulin between 15:00 and 17:00 would be 4 U (i.e., (3.8+4+4.2)/3).

In some embodiments, the standard deviation ("SD") may be also calculated. If the SD falls outside of a pre-defined range or threshold, the average over- or under-delivered amount of insulin for a select time window over a given period of time can be disregarded and no changes will be made, for example, in the basal delivery profile and/or CIR value. For example, if the average of the total sum of CB doses and DS's during a select time window is 5 U over 7 days and the SD threshold is set as 30% of the average, then an SD of less than 3.5 or more than 6.5 will result in no recommendation for basal rate and/or CIR modification. In some embodiments, if the SD falls outside the pre-defined range or threshold, the correction advisor 206 may search within the designated time period (e.g., the 7-day time period based on the average correction delivery that was calculated) for values that largely deviate from the average, omit these values and recalculate the average and SD of the correction delivery. Determining the SD and whether it is within a pre-defined range or threshold may function as validating means (see FIG. 3). In some embodiments, the correction advisor 206 may notify the user via the user interface to disregard the calculation due to the variability of the over- or under-delivered amount of insulin.

As indicated at step 404, the absolute value of the over- or under-delivered amount of insulin (i.e., |CB-DS|) during a time window may be compared to a threshold value. In some embodiments, the threshold value can be an absolute value or a certain percentage of the user's TDD (e.g., 8% of TDD) or total dose for a specific time window. For example, if the total amount of insulin delivered for a time window is 5 U and the threshold value set by the user is 30%, then any sum of CB doses and DS's that exceeds 1.5 U (i.e., 30% of 5 U) may lead to a recommendation for basal rate and/or CIR modification or adjustment. In yet another example, if a user's TDD is 20 U and a threshold value of 10% is selected, then the over- or under-delivered amount of insulin during a time window is checked to determine whether it is greater than 2 U (i.e. 20 U*10%). If the over- or under-delivered amount of insulin during a time window is smaller than the threshold (e.g., 2 U), then no change or action is required (as in step 405). If the absolute value is greater than the threshold (as in step 406), an appropriate action may be executed, such as an adjustment of basal dose (as in steps 407 and 408) or CIR (as in steps 409 and 410).

In some embodiments, the amount of over- or under-delivery (e.g., CB and/or DS) for a time window may be checked relative to meal times (step 406). If the CB dose and/or DS regularly precede a meal or MB dose, then the basal delivery profile for that time window may be adjusted (step 407). If the CB dose and/or DS regularly follow a meal or MB dose, then the CIR value of the time window may be adjusted (step 409). For example, in some embodiments, if a time window comprises both pre-meal and post-meal segments, the correction advisor 206 may check the amount of the CB doses and/or DS commands relative to the MB time and, accordingly, the correction advisor 206 may initiate a recommendation to adjust the basal delivery profile and/or CIR value. For example, if 80% of the CB dose and/or DS commands were given in the post-meal segment, the correction advisor 206 may recommend an adjustment of the CIR value. If the CB doses and/or DS commands were distributed equally between the pre-meal and post-meal segments, the correction advisor 206 may recommend adjusting both the CIR value and the basal delivery profile. In some embodiments, the amount of over- or under-delivery (e.g., CB dose and/or DS) for a time window may be checked relative to meal times. In some embodiments each time window may correspond to either a pre-meal or post-meal segment and, according to the meal segment, the correction advisor 206 may initiate a recommendation.

EXAMPLES

Pre-Meal Segments—Basal Rate Adjustment

If the average pre-meal bolus dose for a particular time window is over or under the programmed amount of insulin delivered, a change in the basal delivery profile for that time window may be required (step 407). The average over- or under-delivered amount of insulin may be distributed (step 408) across the basal rate for that time window by increasing or decreasing the basal rate accordingly. For example if an average over-delivered amount of insulin of a pre meal time window from 15:00-17:00 is 0.5 U and the programmed basal rate is 1.5 U/h, then the basal rate may be adjusted to 1.25 U/h between 15:00-17:00. If the average under-delivered amount of insulin from 15:00-17:00 is 2 U and the programmed basal rate is 1.5 U/h, then the basal rate may be adjusted to 2.5 U/h between 15:00-17:00. If the programmed basal rate was, for example, 1 U/h between 15:00 and 16:00, 2 U/h between 16:00 and 17:00 and the average under-delivered amount of insulin from 15:00-17:00 was 2 U, then the basal rate may be adjusted to 2 U/h between 15:00-16:00 and 3 U/h between 16:00 and 17:00.

Post-Meal Segments—CIR Adjustment

If the average post-meal bolus dose for a particular time window is over or under the programmed amount of insulin delivered, a change in the CIR value for that time window may be required (step 409). The new CIR value is determined at step 410 according to the amount of insulin over- or under-delivered, MB doses and TC for that time window. For example, the new CIR value may be calculated according to the following equation:

$$CIR = \Sigma TC / (\Sigma MB + \Sigma CB - \Sigma DS's)$$

For example, if during a specific post-meal time window the following boluses were delivered: MB=2 U to cover 20 g of carbohydrates (since MB=carbohydrates/CIR then current CIR=20/2=10 g/U); MB=4 U to cover 40 g; CB=1 U; CB=3 U, then the new CIR value in the selected time window would be 6 g/U (60 g/(2 U+4 U+1 U+3 U)). In some embodiments, RI values may be also taken into account in the above mentioned calculation.

In some embodiments, the new CIR value may be determined based on a calculation of the average CIR value in the time window, over a period of time (e.g., 7 days), each CIR value in the period of time may be calculated according the above formula.

In some embodiments, an over- or under-delivered amount of insulin in a post-meal time window may result from an inappropriate CIR value, basal delivery profile or both. In such embodiments the correction advisor 206 may compare the basal delivery profile to another relevant time window which contains only pre-meal segment to verify the accuracy of the basal delivery profile. According to the results of the verification, the correction advisor may initiate a recommendation to modify the CIR value, the basal delivery profile or both.

Figure 5A:
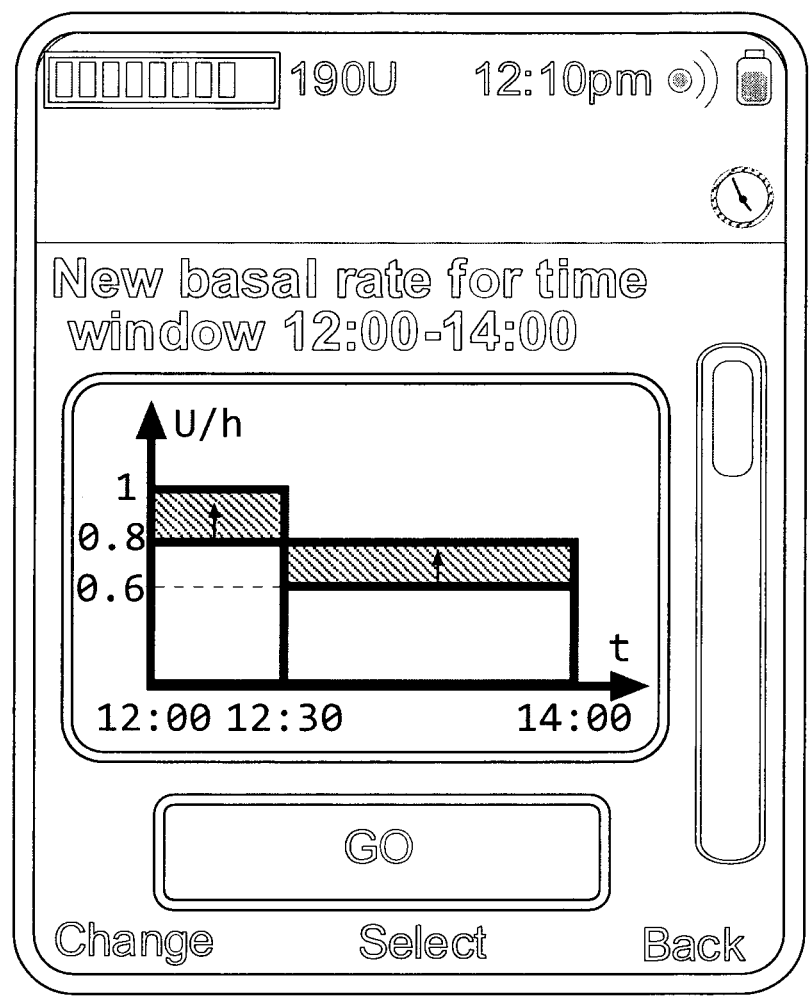
FIGS. 5a-5b illustrate a user interface of a correction advisor, according to some embodiments of the present disclosure.
Figure 5B:
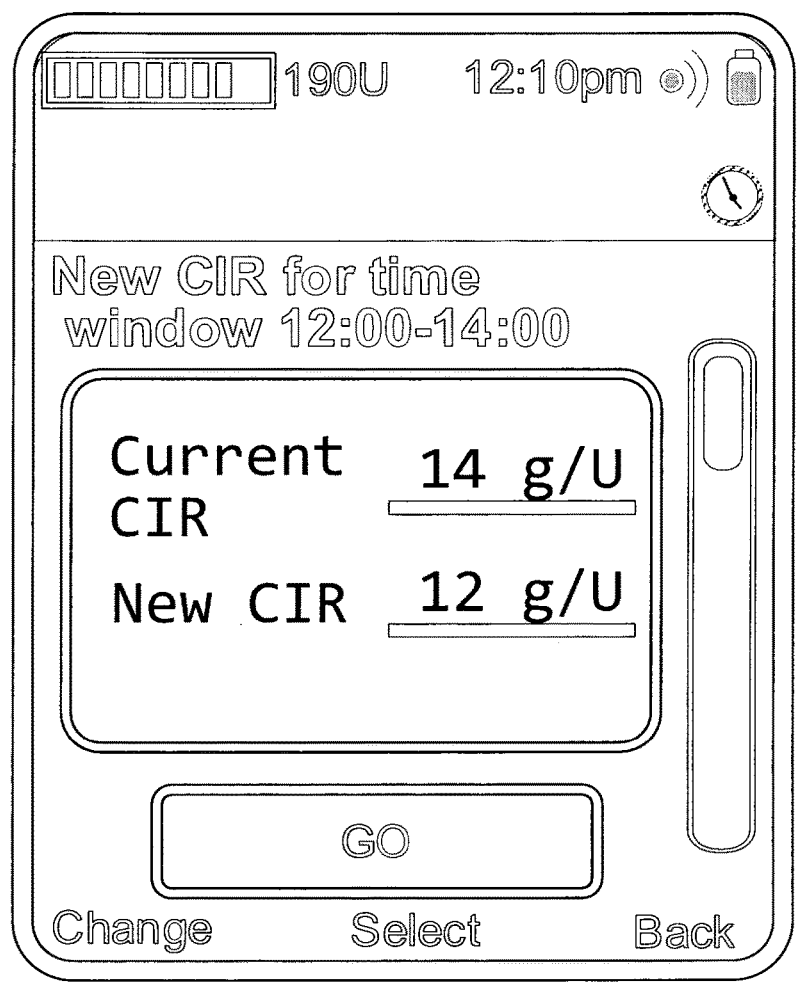

In some embodiments, the amount of over- or under-delivery (e.g., CB and/or DS) in a time window may be further checked relative to influencing scenarios 202b (shown in FIG. 2), such as, physical activity of the user, and modified respectively. FIGS. 5a-5b illustrate examples of a user interface associated with the correction advisor 206. FIG. 5a illustrates an example of a graphical user interface ("GUI") (e.g., implemented in a window, screen or display of a remote control) which presents a modified basal delivery profile. In some embodiments, the GUI may enable the user to adjust the basal delivery profile. As seen in FIG. 5a, the time window may be between 12:00 and 14:00 and include a pre-meal segment. The programmed basal delivery profile may be 0.8 U/h between 12:00 and 12:30 and 0.6 U/h between 12:30 and 14:00. Based on an average under-delivered amount of insulin of 0.4 U, the recommended adjusted basal delivery profile may be 1 U/h between 12:00 and 12:30 and 0.8 U/h between 12:30 and 14:00. This recommendation can be generated by the correction advisor 206. In some embodiments, the modification of the delivery amount and/or rate according to the recommended basal delivery profile may be done by the processor automatically. In some embodiments, the adjustment may require patient confirmation, i.e., the user can accept or reject the recommended basal delivery profile.

FIG. 5b illustrates an example of a GUI which presents a recommendation to the user to adjust the CIR value. The time window in this example is between 12:00 and 14:00 and includes a post-meal segment. As seen in FIG. 5b, based on under-delivery of insulin to cover a carbohydrate load, a lower CIR is recommended for the time window (i.e., between 12:00 and 14:00). Various examples of GUI screens and flows are disclosed in U.S. Provisional Patent Application No. 61/357,870, entitled "User Interface for Infusion Device," the disclosure of which is herein incorporated by reference in its entirety.

Figure 6:
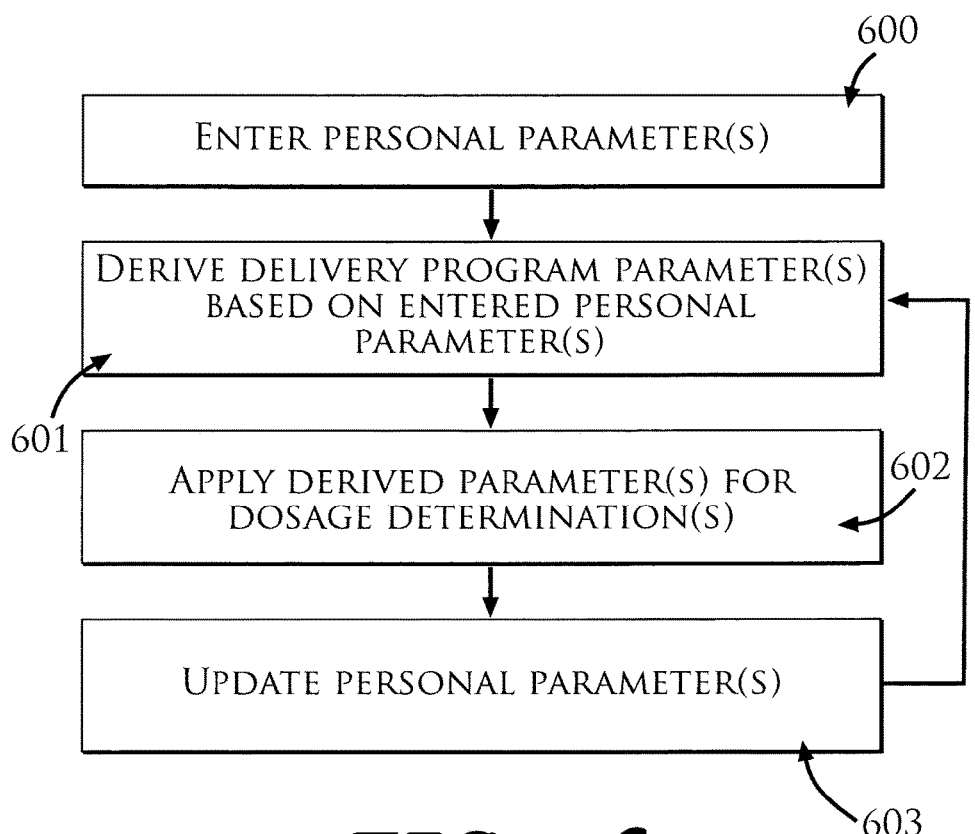
FIG. 6 illustrates a flow diagram of a procedure for deriving the appropriate insulin delivery dose, according to some embodiments of the present disclosure.

FIG. 6 illustrates a flow diagram of an example procedure for deriving at least one delivery program 202a parameter based on personal parameters 204b according to some embodiments (202a and 204b are shown in FIG. 2). Accordingly, in some such embodiments, insulin dosage may be derived from at least one delivery program 202a parameter (or user-specific variable, USV), including without limitation TDD, TBD, CIR and/or IS. These variables may be derived from at least one personal parameter 204b (or user-known parameter, UKP) relating to a user's physical state, such as body weight, BMI, fat percentage, waist circumference, heart rate, blood pressure and maximal oxygen consumption ($VO_2$ max). According to one embodiment, TDD, TBD, IS and CIR may be derived from the user's body weight as follows:

TDD=Body weight×0.5=*TBD*/0.4

*TBD*=Body weight×0.2

CIR=600/Body weight=300/TDD

IS=300/Body weight=1500/TDD

According to some embodiments, TDD (or any other delivery program 202a parameters) may be derived from more than one personal parameter 204b according to the formula:

$$TDD = \sum_{Pk=1}^{Pk=n} Pk$$

where n=number of personal parameters, P=the personal parameter (e.g., body weight) and k=a parameter-related constant (e.g., for ages 10, 20, 30 and 40, k=0.5 (50%), 0.6 (60%), 0.7 (70%), and 0.8 (80%), respectively).

EXAMPLES

A first personal parameter, $P_1$ is body weight with a parameter-related constant $k_1$ of 0.5, 0.6, 0.7, and 0.8 for ages 10, 20, 30, and 40, respectively. A second personal parameter, $P_2$ is resting heart rate with a parameter-related constant $k_2$ of 0.04, 0.05, 0.06, and 0.07 for ages 10, 20, 30 and 40, respectively.

Patient 1:
a. Weight=80 pounds
b. Age=20
c. $k_1$ (for age 20)=0.6
d. Resting heart rate=90
e. $k_2$ (for age 20)=0.05

TDD=(80×0.6)+(90×0.05)=52 U

Patient 2:
a. Weight=80 pounds
b. Age=30
c. $k_1$ (for age 30)=0.7
d. Resting heart rate=90
e. $k_2$ (for age 30)=0.06

TDD=(80×0.7)+(90×0.06)=61.4 U

Accordingly, as shown in FIG. 6, at step 600, at least one known personal parameter 204b of the user may be inputted by the user and/or caregiver via a user interface and/or retrieved from memory and/or received from a remote device (e.g., PC). The personal parameters 204b may include one or more of a user's body weight, BMI, fat percentage, waist circumference, heart rate, blood pressure or maximal oxygen consumption ($VO_2$ max). At step 601, the correction advisor 206 may derive at least one delivery program 202a parameter based on one or more personal parameters 204b entered at step 600. In some embodiments, the derived delivery program 202a parameters may comprise TDD, TBD, CIR and/or IS. In some embodiments, the delivery program 202a parameters may be derived from a database stored in a memory which may include delivery program 202a parameters and corresponding personal parameters 204b. In other embodiments, the correction advisor 206 may use a mathematical function to correlate delivery program 202a parameters and personal parameters 204b. At step 602, the correction advisor 206 may use the derived delivery program 202a parameters to adjust insulin dosages (basal and/or bolus values, ranges and/or profiles) accordingly. In some embodiments, the correction advisor 206 may recommend that the user adjust insulin dosages (basal delivery and/or bolus values, ranges and/or profiles) according to the derived delivery program 202a parameters. In some embodiments, the parameters, variables and/or dosages may be stored in memory. At step 603, upon a change in the user's physical state, the user may input the change via a user interface by updating, for example, the influencing scenarios 202b and/or updating the user's personal parameters 204b. The delivery program 202a parameters may be derived (step 601) from the updated personal parameters and the insulin dosage may be adjusted accordingly. For example, if the known personal parameter 204b used to derive the delivery program 202a parameters is body weight, any loss or gain of weight may be expected to alter the insulin dosage required to maintain glycemic control.

Figure 7:
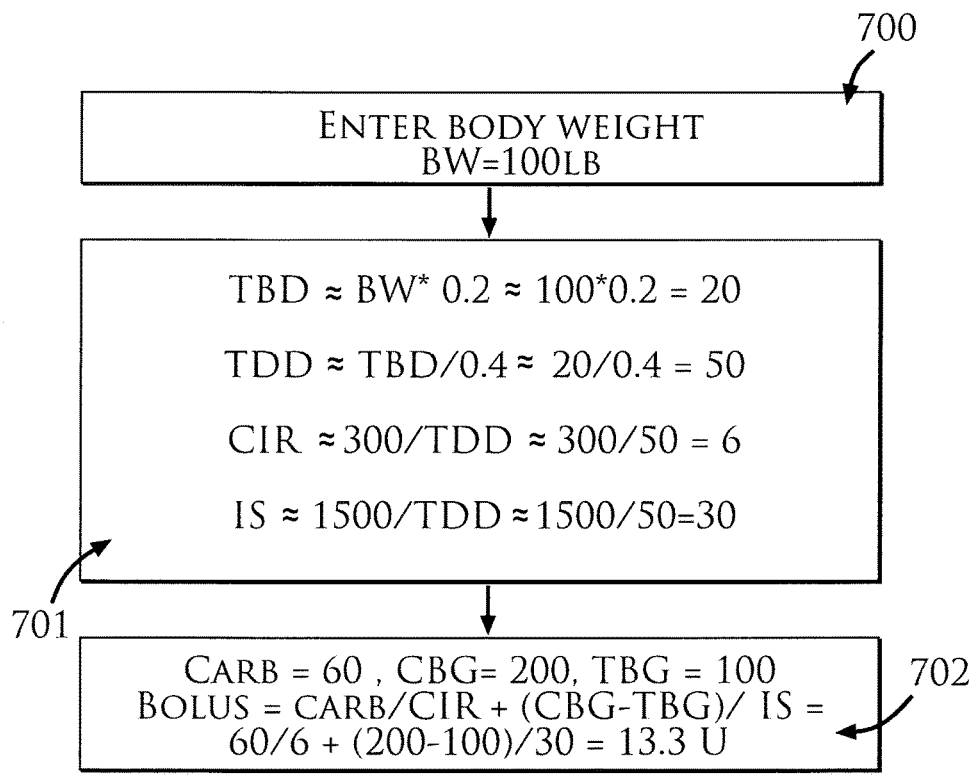
FIG. 7 illustrates a flow diagram of a procedure for deriving the appropriate insulin delivery dose, including a numerical example, according to some embodiments of the present disclosure.

FIG. 7 illustrates an example flow chart for deriving delivery program 202a parameters from a personal parameter 204b and determining suitable insulin dosage. At step 700, a user's body weight may be entered as the user's known physical personal parameter. In the given example, shown in FIG. 7, a body weight of 100 pounds is entered. At step 701, the user's TBD, TDD, IS and CIR can be derived from the user's body weight according to the following formulations (for example):

TBD can be substantially equal to the user's body weight×0.2. In the given example, TBD=20 U (100× 0.2).

TDD can be substantially equal to the TBD/0.4. In the given example, TDD=50 U (20/0.4=50).

CIR can be substantially equal to the 300/TDD. In the given example, CIR=6 g/U (300/50=6).

IS can be substantially equal to the 1500/TDD. In the given example, IS=30 mg/dL per unit of insulin (1500/50=30).

At step 702, a bolus dose may be calculated using the newly-derived parameters in the following formula:

Recommended bolus=[(TC/CIR)+(CBG−TBG)/IS]−RI

In the given example, a bolus of 13.3 U is recommended to cover a meal containing 60 grams of carbohydrates when the current blood glucose is 200 mg/dL and the TBG is 100 mg/dL.

Figure 8:
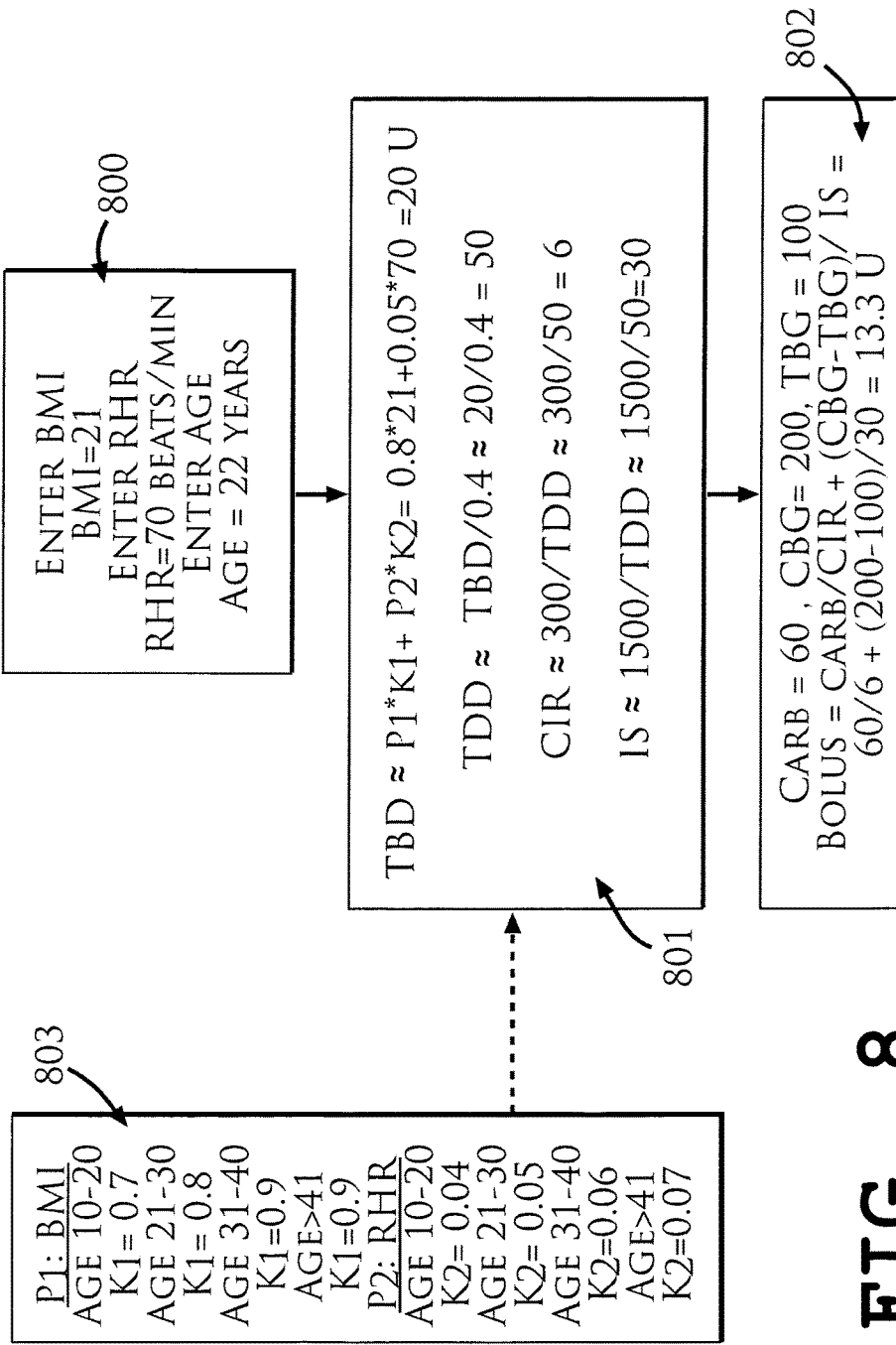
FIG. 8 illustrates a flow diagram of a procedure for deriving the appropriate insulin delivery dose, including a numerical example, according to some embodiments of the present disclosure.

FIG. 8 illustrates an example flow chart for deriving delivery program 202a parameters from three known personal parameters 204b and determining suitable insulin dosage. At step 800, a user's age, BMI, and resting heart rate ("RHR") are entered as the user's known personal parameters. In the given example in FIG. 8, an age of 22 years, BMI of 21 and RHR of 70 are entered. At step 801, the user's TBD, TDD, IS and CIR may be derived from the user's age, BMI and RHR according to the following formulations (for example):

The weight of BMI (parameter, $P_1$) in determination of the user's TBD is a function of age according to a parameter-related constant, $k_1$. $k_1$ for age 22 is 0.8.

The weight of RHR (parameter, $P_2$) in determination of the user's TBD is a function of age according to a parameter-related constant, $k_2$. $k_2$ for age 22 is 0.05.

$$TBD=(P_1 \times k_1)+(P_2 \times k_2)=(0.8 \times 21)+(0.05 \times 70)=20 \text{ U}.$$

TDD can be substantially equal to the TBD/0.4. In the given example, TDD=50 U.

CIR can be substantially equal to the 300/TDD. In the given example, CIR=6 g/U.

IS can be substantially equal to the 1500/TDD. In the given example, IS=30 mg/dL per unit of insulin.

At step 802, a bolus dose may be calculated by using the newly-derived parameters in the formula:

Recommended bolus=[(TC/CIR)+(CBG−TBG)/IS]−RI

In the given example, a bolus of 13.3 U is recommended to cover a meal containing 60 grams of carbohydrates when the current blood glucose is 200 mg/dL and the TBG is 100 mg/dL.

Various embodiments of the subject matter described herein can be realized in digital electronic circuitry, integrated circuitry, specially designed ASICs (application specific integrated circuits), computer hardware, firmware, software, and/or combinations thereof. These various embodiments may include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein can be implemented on a computer having a display device (e.g., a CRT (cathode ray tube), LCD (liquid crystal display) monitor, or other display device) for displaying information to the user and a keyboard and a pointing device (e.g., a mouse or a trackball) by which the user may provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The subject matter described herein can be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system can be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Some embodiments of the present disclosure preferably implement the correction advisor 206 via software operated on a processor contained in a remote control device of an insulin dispensing system and/or a processor contained in an insulin dispensing device being part of an insulin dispensing system.

Any and all references to publications or other documents, including but not limited to, patents, patent applications, articles, Web pages and/or books presented in the present application, are herein incorporated by reference in their entireties.

Although a few variations have been disclosed in detail above, this has been done by way of example for purposes of illustration only, and is not intended to be limiting with respect to the scope of the appended claims, which follow, and other modifications are possible. For example, the logic flow depicted in the accompanying figures and described herein does not require the particular order shown, or sequential order, to achieve desirable results. Other embodiments, implementations, aspects, advantages, and modifications can be considered within the scope of the following claims, as well as claims that can be supported by the current disclosure.

What is claimed is:

1. A method for determining a parameter of a fluid delivery program for a fluid delivery system used by a user and controlling drug delivery by the fluid delivery system to the user, the fluid delivery system comprises:

one or more processors,
memory readable by the one or more processors and storing computer instruction for the fluid delivery program and data, and
a dispensing unit having a dispensing mechanism connected to a cannula that penetrates skin to deliver a therapeutic fluid into subcutaneous tissue of the user, in which operation of the dispensing mechanism of the dispensing unit is controlled by the one or more processors according to the fluid deliver program, the method comprising:
reading from the memory and executing the computer instructions by the one or more processors of the fluid delivery system
retrieving, using one or more processors, the data from the memory, the data corresponding to one or more time windows;
assessing, using one or more processors, a correction delivery for the one or more time windows based on the data;
determining, using one or more processors, a new carbohydrate-to-insulin ratio (CIR) value for the one or more time windows if the correction delivery regularly follows a meal bolus;
determining, using one or more processors, a new basal delivery profile for the one or more time windows if the correction delivery regularly precedes a meal bolus; and
controlling the dispensing mechanism of the dispensing unit by the one or more processors according to the fluid deliver program updated with either the new carbohydrate-to-insulin ratio (CIR) value or the new basal delivery profile to deliver the therapeutic fluid into the subcutaneous tissue of the user.

2. The method of claim 1, wherein:
the data includes a first amount of fluid delivered via one or more correction boluses and a second amount of fluid not delivered due to one or more delivery suspensions; and
the correction delivery is based on, at least in part, a difference between the first amount and second amount of fluid.

3. The method of claim 2, wherein assessing the correction delivery includes subtracting the second amount of fluid from the first amount of fluid.

4. The method of claim 2, wherein assessing the correction delivery comprises averaging the correction delivery of at least two time windows of the one or more time windows, each of the at least two time windows corresponding to the same time period on a different day.

5. The method of claim 4, wherein assessing the correction delivery comprises:
calculating a standard deviation of the average correction delivery; and
determining whether the standard deviation is smaller than a predetermined amount of fluid.

6. The method of claim 4, wherein assessing the correction delivery comprises determining whether the average correction delivery exceeds a predetermined amount of fluid.

7. The method of claim 1, further comprising notifying the user about the determination of the new CIR value and/or new basal delivery profile.

8. The method of claim 1, wherein the new basal delivery profile precedes the one or more time windows for which the correction delivery was assessed to compensate for a lag period between a change in delivery rate and pharmacological effect.

9. The method of claim 2, further comprising enabling inputting, via a user interface, of at least one of the one or more correction boluses and the one or more delivery suspensions.

10. The method of claim 1, wherein the determination of the modification of the new CIR value and/or new basal delivery profile is based on influencing scenarios.

11. The method of claim 1, further comprising validating the correction delivery.

12. The method of claim 3, wherein when the correction delivery regularly follows a meal bolus, the method further comprises determining a new CIR value lower than a programmed CIR value, if a value representative of the result of subtracting the second amount of fluid from the first amount of fluid is higher than zero.

13. The method of claim 3, wherein when the correction delivery regularly follows a meal bolus, the method further comprises determining a new CIR value higher than a programmed CIR value, if a value representative of the result of subtracting the second amount of fluid from the first amount of fluid is lower than zero.

14. The method of claim 3, wherein when the correction delivery regularly precedes a meal bolus, the method further comprises determining a new basal delivery profile higher than a programmed basal delivery profile, if a value representative of the result of subtracting the second amount of fluid from the first amount of fluid is higher than zero.

15. The method of claim 3, wherein when the correction delivery regularly precedes a meal bolus, the method further comprises determining a new basal delivery profile lower than a programmed basal delivery profile, if a value representative of the result of subtracting the second amount of fluid from the first amount of fluid is lower than zero.

16. The method of claim 3, comprising computing the value representative of the result of subtracting the second amount of fluid from the first amount of fluid based on an average of the subtraction.

17. The method of claim 1, further comprising storing, in a memory, the new CIR value and/or new basal delivery profile.

18. The method of claim 1, further comprising initiating delivery of fluid in correspondence with the new CIR value and/or new basal delivery profile.

19. A non-transitory machine-readable medium comprising computer-executable instructions stored thereon, which when executed on a processor, perform the method of determining a parameter of a fluid delivery program for a fluid delivery system used by a user and controlling drug delivery by the fluid delivery system to the user, the method comprising:
retrieving via using the processor, data from memory of the fluid delivery system, the data corresponding to one or more time windows;
assessing via using the processor, a correction delivery for the one or more time windows based on the data;
determining via using the processor, a new carbohydrate-to-insulin ratio (CIR) value for the one or more time windows if the correction delivery regularly follows a meal bolus;
determining via using the processor, a new basal delivery profile for the one or more time windows if the correction delivery regularly precedes a meal bolus; and
controlling via using the processor, a dispensing mechanism of the fluid delivery system according to the fluid deliver program updated with either the new carbohydrate-to-insulin ratio (CIR) value or the new basal delivery profile to deliver the therapeutic fluid into subcutaneous tissue of the user.

20. A method for determining a parameter of a fluid delivery program for a fluid delivery system used by a user, the fluid delivery system comprises:
one or more processors,
memory readable by the one or more processors and storing computer instruction for the fluid delivery program and data, and
a dispensing unit having a dispensing mechanism connected to a cannula that penetrates skin to deliver a therapeutic fluid into subcutaneous tissue of the user, in which operation of the dispensing mechanism of the dispensing unit is controlled by the one or more processors according to the fluid deliver program, the method comprising:
reading from the memory and executing the computer instructions by the one or more processors of the fluid delivery system
retrieving, using the one or more processors, data from the memory, the data corresponding to one or more time windows;
assessing, using the one or more processors, a correction delivery for the one or more time windows based on the data;
determining, using the one or more processors, one or more revised drug delivery parameters based on the correction delivery, wherein a new carbohydrate-to-insulin ratio (CIR) value for the one or more time windows is determined by the one or more processors as one of the revised drug delivery parameters if the correction delivery regularly follows a meal bolus, and a new basal delivery profile for the one or more time windows is determined by the one or more processors as one of the revised drug delivery parameters if the correction delivery regularly precedes a meal bolus; and
modifying present and/or future drug delivery to the user, via the dispensing mechanism of the dispensing unit, based on the determination upon the one or more revised drug delivery parameters if the one or more revised drug delivery parameters do not exceed one or more threshold values.

21. The method of claim 1, further comprising notifying via the one or more processors the user to modify the basal delivery profile with the new basal delivery profile and/or the CIR value with the new CIR value if a total over- or under-delivered amount of insulin exceeds a threshold value.

22. The method of claim 21, wherein the threshold value is set by the user or a caregiver.

23. The method of claim 1, further comprising averaging via the one or more processors an over- or under-delivered amount of insulin over a certain time period and rejecting via the one or more processors the new basal delivery profile and/or the new CIR value if a standard deviation (SD) of the average of the over- or under-delivered amount of insulin does not exceed a pre-defined threshold.

24. The method of claim 23, wherein the certain time period is selected from the range of 4 to 20 days.

25. The method of claim 8, wherein the new basal delivery profile precedes the one or more time windows by an amount of time selected from the range of 30 to 60 minutes.

26. The method of claim 1, wherein the data is historical data relating to one or more past fluid delivery parameters of the user corresponding with the one or more time windows.

27. The method of claim 1, wherein the determining of the new CIR value for the one or more time windows if the correction delivery regularly follows a meal bolus results from a sum of over-delivered and under-delivered amounts of insulin for the one or more time windows over a period of time that is greater than two days being an amount of insulin under-delivered or over-delivered not equal to zero.

28. The method of claim 27, wherein when the correction delivery regularly follows a meal bolus from the sum of over-delivered and under-delivered amounts of insulin for the one or more time windows over the period of time that is greater than two days not being equal to zero, the method further comprises averaging the sum over the period of time by the processor, and presenting by the processor the averaged sum as a recommendation for the new CIR value.

29. The method of claim 27, wherein the period of time is selected from 3 to 7 days.

* * * * *